United States Patent
Arthur et al.

(10) Patent No.: US 11,261,210 B2
(45) Date of Patent: Mar. 1, 2022

(54) GLYCOSYLATED ANTITUMOR ETHER LIPIDS AS NOVEL CANCER STEM CELL CYTOTOXIC AGENTS

(71) Applicant: UNIVERSITY OF MANITOBA, Winnipeg (CA)

(72) Inventors: Gilbert Arthur, Winnipeg (CA); Frank Schweizer, Winnipeg (CA); Pranati Samadder, Winnipeg (CA); Yaozu Xu, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 14/377,551

(22) PCT Filed: Feb. 8, 2013

(86) PCT No.: PCT/CA2013/050105
§ 371 (c)(1),
(2) Date: Aug. 8, 2014

(87) PCT Pub. No.: WO2013/116949
PCT Pub. Date: Aug. 15, 2013

(65) Prior Publication Data
US 2015/0011486 A1 Jan. 8, 2015

Related U.S. Application Data

(60) Provisional application No. 61/596,415, filed on Feb. 8, 2012.

(51) Int. Cl.
| | | |
|---|---|---|
| *C07H 15/14* | (2006.01) | |
| *A61K 31/7028* | (2006.01) | |
| *A61P 35/00* | (2006.01) | |
| *A61K 31/7032* | (2006.01) | |
| *C07H 15/04* | (2006.01) | |
| *C07H 7/02* | (2006.01) | |

(52) U.S. Cl.
CPC ......... *C07H 15/14* (2013.01); *A61K 31/7028* (2013.01); *A61K 31/7032* (2013.01); *A61P 35/00* (2018.01); *C07H 7/02* (2013.01); *C07H 15/04* (2013.01)

(58) Field of Classification Search
CPC .......... C07H 15/14; C07H 15/04; C07H 7/02; A61K 31/7028
USPC ............................................. 514/24, 25, 62
See application file for complete search history.

(56) References Cited

U.S. PATENT DOCUMENTS

2017/0189438 A1* 7/2017 Ogunsina ........... A61K 31/7034

OTHER PUBLICATIONS

Eurukulla et al. (J. Med. Chem. 1996, 39, 1545-1548).*
Visvader et al. (Nature Reviews Cancer 8, 755-768 (Oct. 2008)).*
Sarkar et al. (Minerva Chir. Oct. 2009; 64(5): 489-500).*
Singh et al.; PLoS ONE/www.plosone.org, Nov. 2011, vol. 6 (11), pp. 1-11.*
Samadder et al.; Biochem. Cell Biol. 87: 401-414 (2009).*
Herman et al. (Cell Stem Cell, 1(3), 313-323, Sep. 2007).*
Rybak et al. (Biochimica et Biophysica Acta 1813 (2011) 683-694).*
Trisha Gura's article in Science, November, vol. 278, No. 5340 (Nov. 7, 1997), pp. 1041-1042.*
Samadder et al.(Biochenn. Cell Biol. 87: 401-414 (2009)).*
Chu et al. (Stem Cell Biology and Regenerative Medicine, Ch. 2, pp. 15-36; in A.L. Allan (ed.), Cancer Stem Cells in Solid Tumors, 2011).*
Bapat (Cancer Stem cells: Identification and Targets, 2009).*
Dean, "ABC Transporters, Drug Resistance, and Cancer Stem Cells" J Mammary Gland Biol Neoplasia vol. 14 pp. 3-9 (Year: 2009).*
Eyler et al., "Survival of the Fittest: Cancer Stem Cells in Therapeutic Resistance and Angiogenesis" J Clin Oncol vol. 26 No. 17 pp. 2839-2845 (Year: 2008).*

* cited by examiner

*Primary Examiner* — Eric Olson
(74) *Attorney, Agent, or Firm* — Michael R. Williams; Ryan W. Dupuis; Ade + Company Inc.

(57) ABSTRACT

Glycosylated antitumor ether lipids (GAELs) are effective cytotoxic agents against cancer stem cells. Furthermore, combining GAELs which kill cells by a caspase-independent pathway with agents that kill cells by apoptosis will lead to elimination of the differentiated tumor cells and the undifferentiated cancer stem cells leading to an elimination of the tumor and preventing recurrence.

19 Claims, 12 Drawing Sheets

GLYCOSYLATED ANTITUMOR ETHER LIPIDS AS NOVEL CANCER STEM CELL CYTOTOXIC AGENTS

PRIOR APPLICATION INFORMATION

The instant application claims the benefit of U.S. Provisional Patent Application 61/596,415, filed Feb. 8, 2012.

BACKGROUND OF THE INVENTION

Although there has been progress in diagnosing, treating and managing cancer, there are few treatments for some cancers such as brain, pancreatic and ovarian cancers (1) and even with cancers where treatment results in remission there is often a recurrence of the disease that ultimately results in death. The major classes of drugs used in cancer treatment include antimetabolites, anthracyclines, taxanes, and alkylating agents (Ferguson, L R, Pearson, A E (1996), *The clinical use of mutagenic anticancer drugs. Mut. Res.* 355, 1-12) which basically target proliferating cells. They disrupt cell DNA, prevent DNA synthesis or target microtubules in the cells to stop the cancer cells from dividing. These disruptions induce apoptosis to kill the cells (MacFarlane, M (2009), *Cell death pathways-potential therapeutic targets. Xenobiotica,* 39, 616-624). A major persistent problem with treating cancers with the current crop of chemotherapeutic agents is the problem of drug resistance (Kruh, D G, (2003) *Introduction to resistance to anticancer agents. Oncogene,* 22, 7262-7264; Wong, S T, Goodin, S, (2009). *Overcoming drug resistance in patients with metastatic breast cancer. Pharmacotherapy,* 29, 954-965). Drug resistance may be acquired or intrinsic and this phenomenon has been at the root of the inability to cure cancer. Even targeted antibody based therapies such as trastuzumab (herceptin), are also affected by the phenomenon of drug resistance (Bedard, P L, Cardoso, F, Piccart-Gebhart, M J (2009), *Stemming resistance to HER-2 targeted therapy. J. Mammary Gland Biol. Neoplasia,* 14, 55-66). Several mechanisms are responsible for drug resistance. These include the ability of the cells to pump the chemotherapeutic agents out of the cells through the enhanced expression of efflux pumps, enhanced ability to repair the damaged DNA, resistance to oxidative DNA damage, and intrinsic resistance to death by apoptosis (Bao S, Wu Q, McLendon R E, Hao Y, Shi Q, Hjelmelnd A B, Dewhirst M W, Bigner D D, Rich J N (2006) *Glioma stem cells promote radioresistance by preferential activation of the DNA damage response, Nature* 444, 756-760; Longley, D B, Johnston, P G (2005) *Molecular mechanisms of drug resistance. J. Pathol.,* 205, 275-292; Fulda S, Pervaiz S (2009) *apoptosis signaling in cancer stem cells. Int J Biochem Cell Biol.* 42, 31-38; Soengas, M S, Capodieci, P, Polsky, D, Mora, J, Esteller, M, Opitz-Araya, X, McCombie, R, Herman, J G, Gerlad, W L, Lazebnik, Y A, Cordon-Cardo, C, Lowe, S W, (2001) *Inactivation of the apoptosis effector Apaf-1 in malignant melanoma. Nature,* 409, 207-211; Deming, P B, Schafer, Z T, Tashker, J S, Potts, M B, Deshmukh, M, Kornbluth, S, (2004), *Bcr-Abl-mediated protection from apoptosis downstream of mitochondria c release. Mol. Cell. Biol.* 24, 10289-10299; Schatton T, Murphy G F, Frank N Y, Ymaura K, Waaga-gasser A M, Gasser M, Zhan Q, Jordan S, Duncan L M, Weishaupt C, Fuhlbrigge R C, Kupper T S, Sayegh M H, Frank M H (2008), *Identification of cells initiating human melanomas, Nature* 451, 345-349). These characteristics that render the cells resistant to death by current drugs are believed to be associated with the cancer stem cells (CSCs) or cancer progenitor cells (Garvalov B K, Acker T (2011) *Cancer stem cells: a new framework for the design of tumor therapies, J Mol Med* 89: 95-107). According to CSC theory, CSCs represent the small subpopulation of cancer initiating cells, arising through transformation of stem cells (Visvder J E Lindema G J (2008) *Cancer stem cells in solid tumors: accumulating evidence and unresolved questions, Nat Rev Cancer* 8, 755-768). CSCs have the ability not only to renew the CSC population but also generate differentiated cancer cells that make up the bulk of the tumor. They are therefore the driving force behind the growth and progression of the tumor. CSCs have now been reported in virtually all solid tumors from breast (Al-Hajj M, Wicha M S, Benito-Hernandez A, Morrison S J, Clarke M F (2003), *Prospective identification of tumorigenic breast cancer cells, Proc Natl Acad Sci USA* 100, 3983-3988), colon (Dalerba P, Dylla S J, Park I K, Liu R, Wang X, Cho R W, Hoey T, Gurney A, Huang E H, Simeone D M, Shelton A A, Prmiani G, Castelli C, Clarke M F (2007), *Phenotypic characterization of human colorectal cancer stem cells. Proc Natl Acad Sci USA* 104, 10158-10163; Ricci-Vitani L, Lombardi D G, Pilozzi E, Iffoni M, Todaro M, Lescle C, De Maria R (2007) *Identification and expansion of human colon cancer-initiating cells, Nature* 445, 106-110), brain (Singh S K, Hawkins C, Clarke I D, Squire J A, Bayani J, Hide T, Henkelman R M, Cusimano M D, Dirks P B (2004) *Identification of human brain tumor initiating cells, Nature* 432, 396-401), lung (Eramo A, Lotti F, Sette G, Pilozzi E, Biffoni M, Di Virgilio A, Conticello C, Ruco L, Peschle C, De Maria R (2008), *Identification and expansion of the tumorigenic lung cancer stem cell population, Cell Death Differ* 15, 504-514), mesenchymal (Wu C, Wei Q, Utomo V, Nadesan P, Whetsone H, Kandel R, Wunder J S, Alman B A (2007) *Side population cells isolated from mesenchymal neoplasms have tumor initiating potential Cancer Res* 68, 10051-10059), skin (Malanchi I, Peinado H, Klassen D, Hussenet T, Metzger D, Chambon P, Huber M, Hohl D, Cano A, Birchmeier W et al (2008), *Cutaneous cancer stem cell maintenance is dependent on beta-catenin signaling C, Weisystem, Nature* 452, 650-653), pancreas (Li C, Heidt D G, Dalerba P, Burant C F, Zhang L, Adsay V, Wicha M, Clarke M F, Allies L E (2007), *Identification of pancreatic cancer stem cells, Cancer Res* 67, 1030-1037), head and neck (Prince M E, Sivanandan R, Kaczorowski A, Wolf G T, Kaplan M J, Dalrba P, Weissman I L, Clarke M F, Allies L E (2007) *Identification of a subpopulation of cells with cancer stem cell properties in head and neck squamous cell carcinoma, Proc Natl Acad Sci USA* 104, 973-978), prostate (Collins A T, Berry P A, Hyde C, Stower M J, Maitland N J (2005), *Prospective identification of tumorigenic prostate cancer stem cells, Cancer Res* 65, 10946-10951), melanoma (Schatton T, Murphy G F, Frank N Y, Yamaura K, Waaga-Gasser A M, Gasser M, Zhan Q, Jordan S, Duncan L M, Weishaupt C, Fuhlbrigge R C, Kupper T S, Sayegh M H, Frank M H (2008), *Identification of cells initiating human melanomas, Nature* 451, 345-349), gastric (Takaishi S, Okumura T, Tu S, Wang S S, Shibata W, Vigneshwaran R, Gordon S A, Shimada Y, Wang T C (2009), *identification of gastric cancer stem cells using the cell surfacemarker CD44. Stem Cells* 27, 1006-1020), liver (Ma S, Chan K W, Hu L, Lee T K, Wo J Y, Ng I O, Zheng B J, Guan X Y (2007), *Identification and characterization of tumorigenic liver cancer stem/progenitor cells, Gastroenterology,* 132, 2542-2556), ovarian (Zhang S, Balch C, Chan M W, Lai, H C, Matei D, Schilder J M, Yan P S, Huang T H, Nephew K P (2008) *Identification and characterization of ovarian cancer-initiating cells from primary human tumors, Cancer Res*

68, 4311-4320), and in leukemias (Lane S W, Gilliland D G (2010) *Leukemia stem cells, Sem Cancer Biol* 20, 71-76). Aggressive cancers that are refractory to treatment contain more CSCs and there is correlation between the presence of cancer stem cell markers with clinical progression and clinical outcome (Garvalov B K, Acker T (2011) *Cancer stem cells: a new framework for the design of tumor therapies, J Mol Med* 89: 95-107). CSCs have enhanced ability to resist death by chemotherapy or radiotherapy (Hermann P C, Huber S L, Herrler T, Aicher A, Ellwart J W, Guba M, Bruns C J, Heeschen C (2007)*Distinct populations of cancer stem cells determine tumor growth and metastatic activity in human pancreatic cancer, Cell Stem Cell* 1, 313-323; Eramo A, Ricci-Vitiani L, Zeuner A, Pallini R, Lotti F, Sette G, Pilozzi E, Larocca L M, Peschle C, De Maria R (2006), *Chemotherapy resistance of gioblstoma stem cells. Cell death Differ* 13, 1238-1241; Li X, Lewis M T, Huang J, Gutierrez C, Osborne C K, Wu M F, Hilsenbeck S G, Pvlick A, Zhang X, Chamness G C Wong H, Rosen J, Chang J C (2008), *Intrinsic resistance of tumorigenic breast cancer cells to chemotherapy. J Natl Cancer Inst* 100, 672-679).

The CSC theory is a very attractive one that provides an explanation for the relapse or recurrence that often accompanies chemotherapy and radiotherapy. As a consequence of the intrinsic or induced mechanisms that resist cell death by apoptosis, and the ability of the CSCs to remain in Go phase, they survive chemotherapy and radiotherapy which kill the cells of the bulk tumor. The treatments in effect select for these cells. Their unlimited proliferation potential allows them to regenerate the tumor again with differentiated cells after cessation of treatment, thus causing the recurrence of the tumor. In vivo studies have demonstrated an enrichment of CSCs in tumors subjected to irradiation or chemotherapy (Eramo A, Ricci-Vitiani L, Zeuner A, Pallini R, Lotti F, Sette G, Pilozzi E, Larocca L M, Peschle C, De Maria R (2006), *Chemotherapy resistance of gioblstoma stem cells. Cell death Differ* 13, 1238-1241; Bao S, Wu Q, McLendon R E, Hao Y, Shi Q, Hjelmelnd A B, Dewhirst M W, Bigner D D, Rich J N (2006) *Glioma stem cells promote radioresistance by preferential activation of the DNA damage response, Nature* 444, 756-760). CSCs isolated from tumors by sorting for CSC markers have shown greater propensity to survive treatment with chemotherapeutic agents compared to unsorted cells (Garvalov B K, Acker T (2011) *Cancer stem cells: a new framework for the design of tumor therapies, J Mol Med* 89: 95-107). CSCs have also been implicated as the driving force underpinning metastases (Mani S A, Guo W, Liao M J, Eaton E N, Ayyanan A, Zhou A Y, Brooks M, Rheinhard F, Zhang C C, Shipitsin M et al (2008), *The epithelial-mesenchymal transition generates cells with properties of stem cells, Cell* 133, 704-715; Balic M, Lin H, Young L, Hawes D, Giuliano A, McNamara G, Datar R H, Cote R J (2006), *Most early disseminated cancer cells detected in bone marrow of breast cancer patients have a putative breast cancer stem cell phenotype, Clin Cancer res* 12, 5615-5621; Hermann P C, Huber S L, Herrler T, Aicher A, Ellwart J W, Guba M, Bruns C J, Heeschen C (2007) *Distinct populations of cancer stem cells determine tumor growth and metastatic activity in human pancreatic cancer, Cell Stem Cell* 1, 313-323; Pang R, Law W L, Chu A C Y, poon J T, Lam C S C, Chow A K M, Ng L, Cheung L W H, Lan H Y et al (2010), *A subpopulation of CD26+ cancer stem cells with metastatic capacity in human colorectal cancer, Cell Stem Cell* 6, 603-615).

There is now widespread realization that tackling the two major problems associated with cancer therapy, namely drug resistance and metastases, will require strategies that target and eliminate the CSCs (Garvalov B K, Acker T (2011) *Cancer stem cells: a new framework for the design of tumor therapies, J Mol Med* 89: 95-107). This may be achieved by directly killing the CSCs, inducing differentiation with loss of CSC characteristics, or disrupting the niche signals they require for maintenance. Pathways recognized to be important for the CSC self-renewal such as Wnt, hedgehog, and Notch signaling pathways have been targeted in efforts to either kill the CSCs or induce them to differentiate with the loss of CSC characteristics (Garvalov B K, Acker T (2011) *Cancer stem cells: a new framework for the design of tumor therapies, J Mol Med* 89: 95-107). Efforts are also underway to perturb the niche preferred by CSCs; they involve the use of angiogenesis inhibitors and manipulation of hypoxia-induced signaling mechanisms (Bergers G, Hanahan D (2008) *Modes of resistance to antiangiogenic therapy, Nat Rev Cancer* 8, 592-603; Poon E, Harris A L, Ashcroft M (2009) *Targeting the hypoxia-inducible factor (HIF) pathway in cancer, Expert Rev Mol Med* 11, e26).

Since CSCs appear to be intrinsically resistant to apoptosis, agents that kill cells by apoptosis-independent mechanism may be effective in killing CSCs and thus prevent recurrence of the tumor. Very few pharmacological agents that kill CSCs directly have been described. The availability of such compounds may ultimately prevent the recurrence of tumors and provide the basis for a cure.

SUMMARY OF THE INVENTION

According to an aspect of the invention, there is provided a method of killing cancer stem cells and cancer stem cell spheroids by administering an effective amount of a compound selected from the group consisting of:

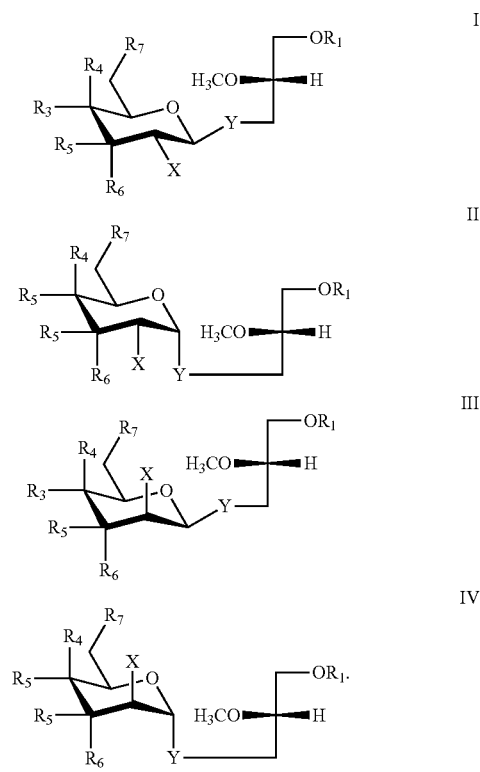

-continued

X = OH, NH$_2$, N$_3$, NHR$_8$, NHC(NH)NH$_2$, N(R$_9$)$_3^+$
Y = O, S, Si(R$_{10}$)$_2$, CH$_2$, NCOR$_2$
R$_1$ = C$_n$H$_{2n+1}$; C$_n$H$_{2n-1}$; C$_n$H$_{2n-3}$; C$_n$H$_{2n-5}$; [n = 10, 11, .....30]
R$_2$ = alkyl (CH$_2$, C$_2$H$_5$, ....., C$_{30}$H$_{61}$), benzyl, aryl
R$_3$ = H; R$_4$ = OH, H
R$_3$ = OH, H; R$_4$ = H
R$_5$ = OH, H; R$_6$ = H
R$_5$ = H; R$_6$ = OH, H
R$_7$ = OH, H, NH$_2$, NHC(NH)NH$_2$, N(R$_9$)$_3^+$
R$_8$ = alkyl, benzyl, aryl,
R$_9$ = alkyl (CH$_3$, C$_2$H$_5$,....C$_{10}$H$_{21}$)
R$_{10}$ = H, alkyl, benzyl, aryl In a further aspect of the invention, there is provided a method of treating a cancer that is refractory to treatment with existing apoptosis-inducing agents comprising administering to an individual in need of such treatment an effective amount of a GAEL as defined above.

In a preferred embodiment, the cancer is selected from cancers that are very refractory to current treatments and have no effective drugs including but not limited to cancers such as pancreatic cancer, ovarian cancer, small cell lung cancer, liver cancer and brain cancer.

Examples of other suitable cancers include but are by no means limited to: drug-resistant cancers originating from any tissue (cancers that initially respond and then develop resistance to apoptosis-inducing drugs); recurring cancers (cancers that respond to treatment (surgery/chemotherapy/radiotherapy) and after a while recur), and metastasized or advanced stage cancers (which usually receive palliative care).

According to a further aspect of the invention, there is provided use of any one of the above-described compounds for killing cancer stem cells and cancer stem cell spheroids.

According to another aspect of the invention, there is provided use of any one of the above-described compounds for treating a cancer that is refractory to treatment with existing apoptosis-inducing agents.

According to an aspect of the invention, there is provided a method of killing cancer stem cells and cancer stem cell spheroids by administering an effective amount of a compound as described above.

According to another aspect of the invention, there is provided the use of any one of the above-described compounds for use as a medicament for treating a cancer that is refractory to treatment with existing apoptosis-inducing agents.

According to yet another aspect of the invention, there is provided any one of the above-defined compounds for use in the treatment of cancer, for example, a cancer that is refractory to treatment with existing apoptosis-inducing agents

BRIEF DESCRIPTION OF THE DRAWINGS

Structures of compounds that have been tested and their abbreviations are to be found below.

Figure 7B:
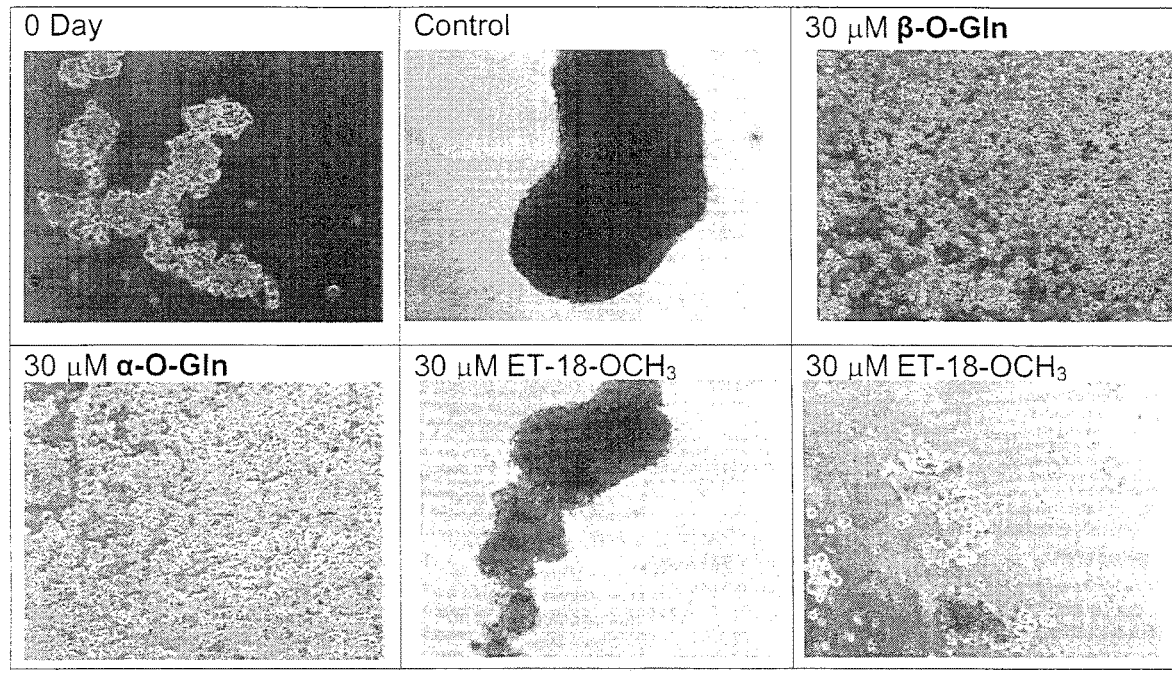
Figure 7A:
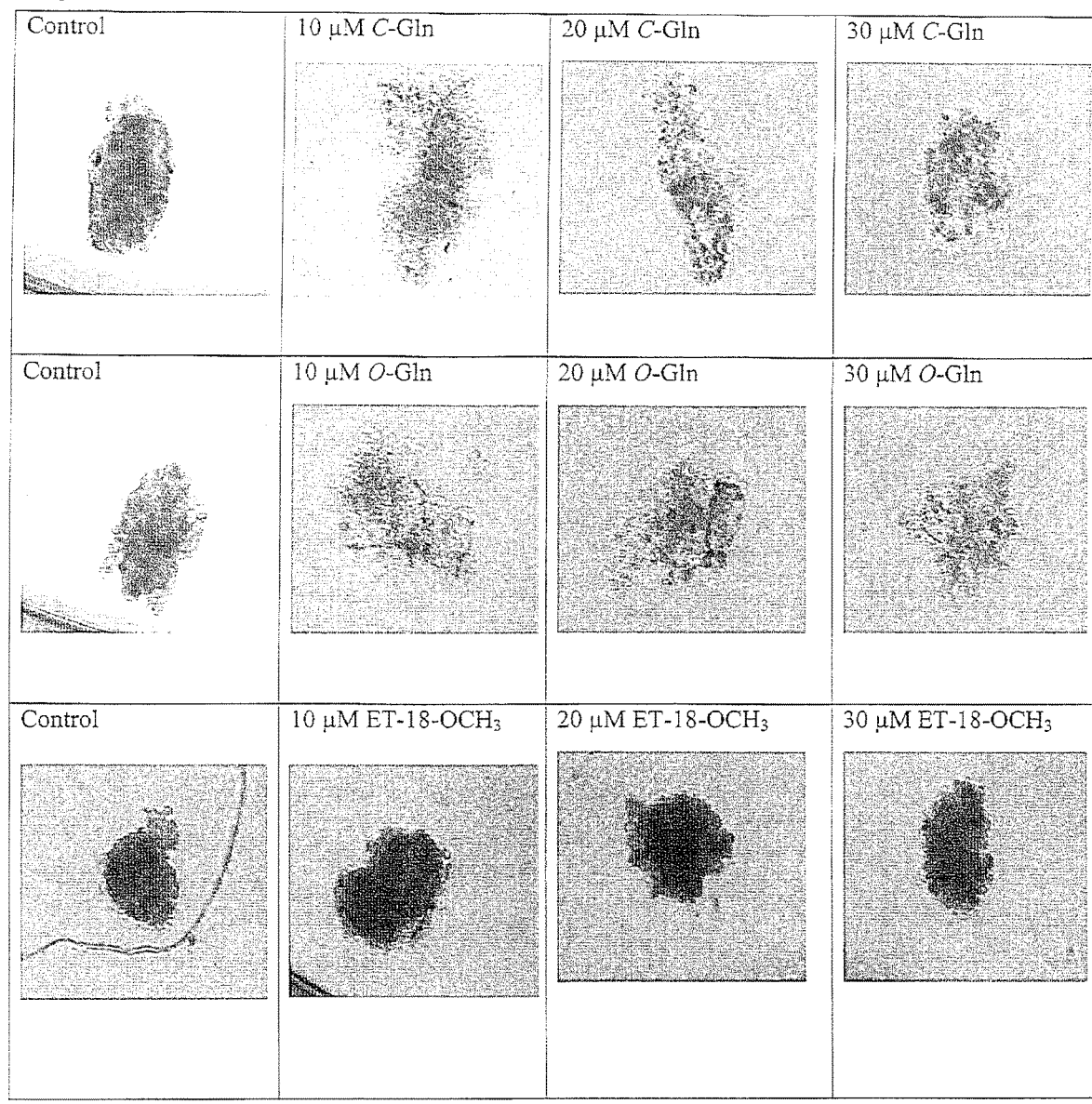

FIG. 7. A. Effect of β-O-Gln, β-C-Gln or ET-18-$OCH_3$ on morphology of JIMT-1 stem cell spheroids. B. Effect of β-O-Gln, α-O-Gln or ET-18-$OCH_3$ on morphology of JIMT-1 stem cell spheroids. JIMT-1 cancer stem cells were grown for 7 days in ultra low adhesion 6 well plates. The tumorspheres formed were harvested, trypsinised and cell numbers were determined. Equal numbers of cells were dispersed into 48-well non-treated plates in mammocult medium and incubated in a $CO_2$ incubator under static conditions. After spheres were formed, O-Gln, C-Gln or ET-18-$OCH_3$ were added (0, 10, 20 and 30 μM) and incubation was for a total of 6 days with media supplementation after 3 days. Images for FIG. 7A were taken at day 0 and after 72 h following addition of the compounds. Images for FIG. 7B were taken after 6 days incubation with the compounds.

Figure 8:
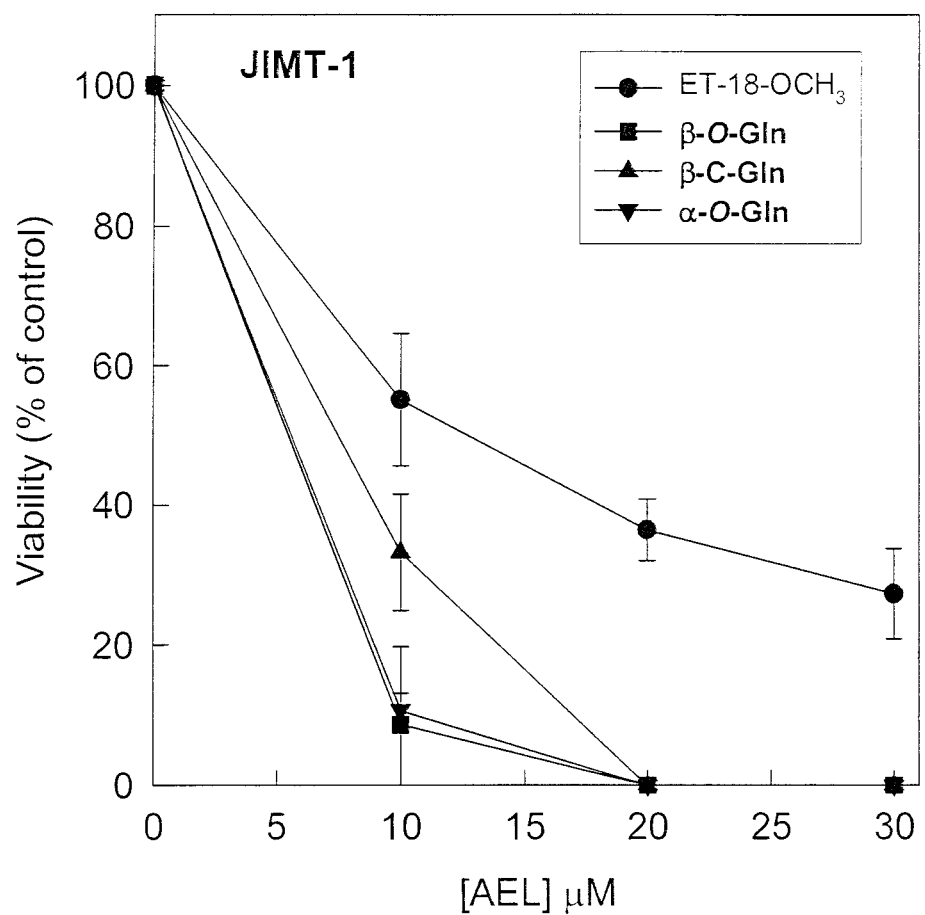

FIG. 8. Effect of β-O-Gln, α-O-Gln, β-C-Gln and ET-18-$OCH_3$ on the viability of JIMT1 stem cell tumorspheres. BT-474 cancer stem cells were grown for 7 days in ultra low adhesion 6-well plates. The tumorspheres formed were harvested, trypsinised and cell numbers were determined. Equal numbers of cells were dispersed into 48-well non-treated plates in mammocult medium and incubation was under static conditions. Wells with only medium but no cells were treated in an identical manner to serve as blanks. After spheres were formed, O-Gln, C-Gln or ET-18-$OCH_3$ (0, 10, 20, 30 μM) were added and incubation was for a total of 6 days. At the end of the incubation, the MTS reagent was added to each well and the plates were mixed in a nutator in a 5% $CO_2$ incubator for 4 h. The absorbance of each well was read at 470 nm. The results are the means±standard deviation of 4 independent determinations.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Herein, the inventors demonstrate that glycosylated antitumor ether lipids or GAELs are effective cytotoxic agents against cancer stem cells. Furthermore, combining GAELs which kill cells by a caspase-independent pathway with agents that kill cells by apoptosis will lead to elimination of the differentiated tumor cells and the undifferentiated cancer stem cells leading to an elimination of the tumor and preventing recurrence.

Non-phosphorylated containing glycosylated antitumor ether lipids, hereinafter referred to as GAELs have a sugar moiety instead of the phosphorylcholine residue found in the C-3 position of the alkyllysophospholipid class of AELs typified by 1-O-octadecyl-2-O-methyl-glycerophosphocholine (edelfosine, ET-18-$OCH_3$).

GAELs, along with alkyllysophospholipids (ALP) and alkylphosphocholines (APC) make up the antitumor ether lipids (AELs). AELs are long-lived analogs of lysophosphatidylcholine and possess antitumor activity (Lohmeyer M, Bittman R (1994) *Antitumor ether lipids and alkylphosphocholines. Drugs Fut* 19, 1021-1037; Brachwitz H, Vollgraf C (1995). *Analogs of alkyllysophospholipids: chemistry, effects on molecular level and their consequences for normal and malignant cells. Pharmacol Ther Rev* 66, 39-82; Bittman R, Arthur G (1999). *Antitumor ether lipids: Biological and biochemical effects, in Liposomes: Rationale design* (A S Janoff ed) Marcell Dekker, New York pp125-144). ALPs (eg ET-18-$OCH_3$) and alkylphosphocholines (eg hexadecyl phosphocholine, miltefosine) kill cells via apoptosis (Ruiter G A, Zerp S F, van Blitterswijk W J, Verheij M (1999). *Alkyllysophospholipids activate the SAPK/JNK pathway and enhance radiation induced apoptosis. Cancer Res* 59, 2457-2463; Gajate C, Santos-Beneit A, Modolell M, Mollinedo F (1998). *Involvement of c Jun NH2-terminal kinase activation and c-jun in the induction of apoptosis by the ether lipid 1-O-octadecyl2-O-methyl glycerophosphocholine. Mol Pharmacol* 53, 602-612; Smets L A, Van Rood H, Salmons G S (1999). *Signaling steps in apoptosis by ether lipids. Apoptosis* 4, 419-427).

GAELs have a sugar residue in place of the phosphorylcholine head group at the C-3 position in ALPs and they inhibit the growth and kill a wide range of cancer cell lines (Guivisdalsky P N, Bittman R, Smith Z, Blank M L, Snyder F, Howard S, Salari H (1990). *Synthesis and antineoplastic properties of ether-linked thioglycolipids. J Med Chem* 33, 2614-2621; Lu X, Rengan K, Bittman R, Arthur G (1994). *The α and β anomers of 1-O-hexadecyl-2-O-methyl-3-S-thioglucosyl-sn-glycerol inhibit the proliferation of epithelial cancer cell lines. Oncol Rep* 1, 933-936; Erukulla R K, Zhou X, Samadder P. Arthur G, Bittman R (1996). *Synthesis and evaluation of the antiproliferative effects of 1-O-hexadecyl-2-O-methyl-3-O-(2'-acetamido-2'-deoxy-β-D-glucopyranosyl)-sn-glycerol and 1-O-hexadecyl-2-O-methyl-3-O-(2'-amino-2'deoxy-β-D-glucopyranosyl)-sn-glycerol on epithelial cancer cell growth. J Med Chem* 39, 1541-1548; Samadder P, Byun H-S, Bittman R, Arthur G (1998). *Glycosylated antitumor ether lipids are more effective against oncogene-transformed fibroblasts than choline-containing alkyl-lysophospholipids. Anticancer Res.* 18, 465-470 (1998); Yang G, Franck R W, Bittman R, Samadder P, Arthur G (2001). *Synthesis and growth-inhibitory properties of glucosamine-derived glycerolipids. Org. Lett.* 3, 197-200; Marion-Albemas J R, Bittman R, Peters A, Mayhew E (1996). *Synthesis and growth inhibitory properties of glycosides of 1-O-hexadecyl-2-O-methyl-sn glycerol analogs of the antitumor ether lipid ET-18-OCH3 (edelfosine). J. Med Chem.* 39, 3241-3247). The two most effective GAELs are 1-O-hexadecyl-2-O-methyl-3-O-(2'-amino-2'-deoxy-β-D-glucopyranosyl)-sn-glycerol, (Gln) and its C-glycoside analog (C-Gln) (Erukulla R K, Zhou X, Samadder P. Arthur G, Bittman R (1996). *Synthesis and evaluation of the antiproliferative effects of 1-O-hexadecyl-2-O-methyl-3-O-(2'-acetamido-2'-deoxy-β-D-glucopyranosyl)-sn-glycerol and 1-O-hexadecyl-2-O-methyl-3-O-(2'-amino-2'-deoxy-β-D-glucopyranosyl)-sn-glycerol on epithelial cancer cell growth. J Med Chem* 39, 1541-154; Yang G, Franck R W, Bittman R, Samadder P, Arthur G (2001). *Synthesis and growth-inhibitory properties of glucosamine-derived glycerolipids. Org. Lett.* 3, 197-200). We have recently synthesized and compared the cytotoxicity of α anomer of O-(α-AO2) and S-Gln (α-AS2) to β-O-Gln (β-AO1). The results revealed the α-O-Gln (α-AO2) to have superior activity relative to α-O-Gln (β-AO1). The S-anomers (α-AS2 and β-AS1) were however not as active as β-O-Gln (Xu, Y., Ogunsina, M., Samadder, P., Arthur, G.; Schweizer, F (2013). Structure-activity relationships of glucosamine-derived glycerolipids: the role of the anomeric linkage, the cationic charge and the glycero moiety on the antitumor activity. ChemMedChem in press). The C-glycosidic bond is less susceptible to metabolism hence C-Gln (β-AC1) is expected to have a longer half-life than O-Gln in vivo.

The inventors recently showed that GAELs kill cells by a lysosomal-mediated caspase-independent cell death pathway (Samadder P, Bittman R, Byun-H-S, Arthur G (2009). *A glycosylated antitumor ether lipid kills cells by a paraptosis-like cell death. Biochem Cell Biol* 87, 401-414 Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-846). Gln killed cells devoid of caspases 9 and 3, Apaf1 and ASK1. In cells with a functioning apoptotic pathway, cell death occurred without activation of caspase 3 or 9 (Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-846) and incubation of cells with the pan caspase inhibitor zVADFMK, had no effect on Gln-induced cell death. Gln does not induce loss of mitochondria membrane permeability (MMP) or cytochrome C leakage into the cytosol, and nor was cleavage of Bid observed (Samadder P, Bittman R, Byun-H-S, Arthur G (2009). *A glycosylated antitumor ether lipid kills cells by a paraptosis-like cell death. Biochem Cell Biol* 87, 401-414; Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-84663). Incubation of cells with GAELs results in a massive accumulation of cytoplasmic vacuoles with lysosomal characteristics that increase in size and number with incubation time and precedes death. This phenomenon is unrelated to autophagy as it was observed in both autophagy competent and autophagy-incompetent cells (Samadder P, Bittman R, Byun-H-S, Arthur G (2009). *A glycosylated antitumor ether lipid kills cells by a paraptosis-like cell death. Biochem Cell Biol* 87, 401-414).

The inventors have recently demonstrated that the large acidic vacuoles are generated as a consequence of the perturbation of the endocytosis pathway (Samadder P, Byun H-S, Bittman R, Arthur G (2011) *The endocytosis pathway is required for the cytotoxic effects of glycosylated antitumor ether lipids, Anticancer Res* 31, 3809-3818) and that GAELs are not lysomotropic agents as was previously postulated (Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-84663). Furthermore an active endocytosis pathway was essential for GAEL activity (Samadder P, Byun H-S, Bittman R, Arthur G (2011) *The endocytosis pathway is required for the cytotoxic effects of glycosylated antitumor ether lipids, Anticancer Res* 31, 3809-3818). The generation of the large acidic vacuoles is a hallmark of this non-apoptosis death pathway induced by GAELs. We have observed the generation of these vacuoles by α-O-Gln, and the thio analogues (Xu, Y., Ogunsina, M., Samadder, P., Arthur, G.; Schweizer, F. Structure-activity relationships of glucosamine-derived glycerolipids: the role of the anomeric linkage, the cationic charge and the glycero moiety on the antitumor activity. ChemMedChem in press.) and also with the very active α-O-Galn analogue.

The correlation between the generation of the large acidic vacuoles with lysosomal characteristics and cell death led us to investigate whether cell death could be mediated by cathepsins. Our results showed that cytosolic cathepsin levels were significantly greater in Gln treated cells relative to controls and furthermore the cathepsin inhibitor, pepstatin A, attenuated Gln-induced cell death (Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-84663). It is worth noting that GAEL-induced cell death is not by necrosis as the cells treated with these compounds remain intact and rounded even when not viable. Cathepsin mediation of cell death is known (Boya P, Andreau K, Poncet D, Zamzami N, Perfettini J L, Metivier D Ojcius D M, Jaattela M, Kroemer G (2003). *Lysosomal membrane permeabilization induces cell death in a mitochondrion-dependent fashion. J Exp Med* 197, 1323-1334; Kirkegaard T, Jaattela M (2008). *Lysosomal involvement in cell death and cancer. Biochim Biophys Acta.* 1793, 746-754; Foghsgaard L, Wissing D, Mauch D, Lademann U, Bastholm L, Boes M et al (2001). *Cathepsin B acts a dominant execution protease in tumor cell apoptosis induced by tumor necrosis factor. J Cell Biol* 153, 999-1009), although the mechanism downstream was deemed to be via action on t-Bid to activate caspase-dependent apoptosis (Bidere N, Lorenzo H K, Carmona S, Lafarge M, Harper F, Dumont C, Senik A (2003) *Cathepsin D triggers Bax activation resulting in selective apoptosis-inducing factor relocation in T lymphocytes entering early commitment phase to apoptosis J Biol Chem* 278, 31401-31411; Guicciardi M E, Deussing J, Miyoshi H, Bronk S F, Svingen P A, Peters C. Kaufmann S H, Gores G J (2000), *Cathepsin B contributes to TNF TNF-alpha mediated hepatocyte apoptosis by promoting mitochondrial release of cytochrome C. J Clin Invest* 106, 1127-1137) or caspase-independent apoptosis (Lockshin R A, Zackeri Z (2002). *Caspase-independent cell deaths. Curr Opin Cell Biol* 14, 727-733; Bidere N, Lorenzo H K, Carmona S, Laforge M, Harper F, Dumont C, Senik A (2003) *Cathepsin D triggers Bax activation resulting in selective apoptosis-inducing factor relocation in T lymphocytes entering early commitment phase to apoptosis J Biol Chem* 278, 31401-31411; Guicciardi M E, Deussing J, Miyoshi H, Bronk S F, Svingen P A, Peters C. Kaufmann S H, Gores G J (2000). *Cathepsin B contributes to TNF-alpha mediated hepatocyte apoptosis by promoting mitochondrial release of cytochrome C, J Clin Invest* 106, 1127-113723-25b, Boya P and Kroemer G (2008). *Lysosomal membrane permeabilization in cell death. Oncogene* 27, 6431-6451; Stoka V, Turk V, Turk B (2007)*Lysosomal cysteine cathepsins: signaling pathways in apoptosis. Biol Chem* 388, 555-560). In the case of Gln we have shown that Gln does not induce Bid cleavage nor loss of mitochondrial membrane potential (Jahreiss L, Renna M, Bittman R, Arthur G, Rubinsztein D C (2009). *1-O-hexadecyl-2-O-methyl-3-O-(2"acetamido-2"-deoxy-β-D-glucopyranosyl)-sn-glycerol (Gln) induces cell death with more autophagosomes which is autophagy-independent. Autophagy* 5, 835-84663; Samadder P, Bittman R, Byun-H-S, Arthur G (2009). *A glycosylated antitumor ether lipid kills cells by a paraptosis-like cell death. Biochem Cell Biol* 87, 401-414) and is therefore apoptosis independent. Thus, GAEL induced cell death is a novel caspase-independent mitochondria-independent pathway especially as loss of mitochondrial membrane potential is not required.

According to an aspect of the invention, there is provided a method of killing cancer stem cells and cancer stem cell spheroids by administering an effective amount of a compound selected from the group consisting of:

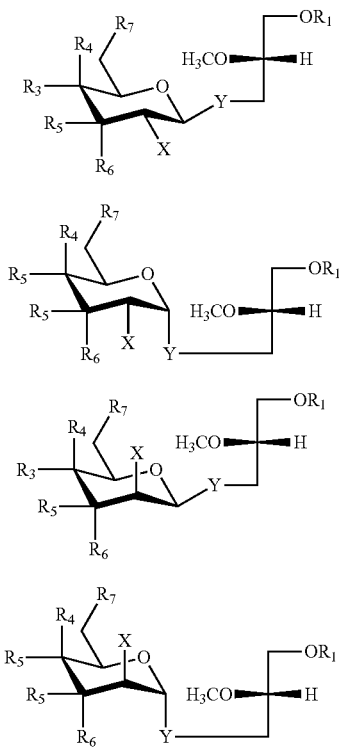

X = OH, NH$_2$, N$_3$, NHR$_8$, NHC(NH)NH$_2$, N(R$_9$)$_3^+$
Y = O, S, Si(R$_{10}$)$_2$, CH$_2$, NCOR$_2$
R$_1$ = C$_n$H$_{2n+1}$; C$_n$H$_{2n-1}$;C$_n$H$_{2n-3}$; C$_n$H$_{2n-5}$; [n = 10, 11, .....30]
R$_2$ = alkyl (CH$_2$, C$_2$H$_5$, ....., C$_{30}$H$_{61}$), benzyl, aryl
R$_3$ = H; R$_4$ = OH, H
R$_3$ = OH, H; R$_4$ = H
R$_5$ = OH, H; R$_6$ = H
R$_5$ = H; R$_6$ = OH, H
R$_7$ = OH, H, NH$_2$, NHC(NH)NH$_2$, N(R$_9$)$_3^+$
R$_8$ = alkyl, benzyl, aryl,
R$_9$ = alkyl (CH$_3$, C$_2$H$_5$,....C$_{10}$H$_{21}$)
R$_{10}$ = H, alkyl, benzyl, aryl As will be apparent to one of skill in the art, two possibilities are provided in the formula above for R$_3$, R$_4$, R$_5$ and R$_6$. These represent subtle modifications on the sugar moiety. For example, R$_3$=OH and R$_4$=H produces glucose while R$_3$=H and R$_4$=OH produces galactose.

In an alternative embodiment, there is provided a method of treating a cancer that is refractory to treatment with existing apoptosis-inducing agents comprising administering to an individual in need of such treatment an effective amount of a GAEL as defined above. As will be appreciated by one of skill in the art, an "effective amount" will depend on many factors, including the age and condition of the patient, the type of cancer and the severity thereof. It is further noted that such an "effective amount" can be determined through routine experimentation.

In a preferred embodiment, the cancer is selected from the group consisting of pancreatic cancer, ovarian cancer, small cell lung cancer, liver cancer and brain cancer. As will be appreciated by one of skill in the art, these types of cancers represent ones which are notoriously difficult to treat and for which there are currently no effective treatments. It is important to note that any suitable cancer may be treated with an effective amount of the GAELs, as discussed herein.

Examples of some suitable cancers include but are by no means limited to: drug-resistant cancers (cancers that initially respond and then develop resistance to apoptosis-inducing drugs); recurring cancers (cancers that respond to treatment (surgery/chemotherapy/radiotherapy) and after a while recur), and metastasized or advanced stage cancers (which usually receive palliative care).

As will be appreciated by one of skill in the art, the GAELS represent known compounds that are not currently being used for treatment. However, as discussed herein, once the inventors discovered its mechanism of action was apoptosis-independent, it was clear that GAELS provide a means to kill the cancer stem cells. As discussed herein, this has been proven to be correct. Accordingly, it was not previously known that GAELs were compounds that killed cells by a caspase and apoptosis independent pathway and therefore that they would represent a means to kill cancer stem cells.

The ability of GAELs to kill cells by a caspase-independent apoptosis-independent pathway indicates these compounds can circumvent the intrinsic resistance to apoptosis displayed by CSCs provided the CSCs did not possess mechanisms to overcome the perturbations caused by the GAEL. GAELs thereby provide a means to kill CSCs so that when used in combination with compounds that kill the bulk tumor cells or removal of the tumor bulk by surgery, the tumor could be eradicated without any recurrence.

The inventors demonstrate that GAELs are small molecules that (1) inhibit the development of cancer stem cell into tumorspheres; (2) cause the disintegration of cancer stem cell spheroids and (3) cause the total loss of viability of cancer stem cells in the spheroids.

There are provided methods of use of compounds having a formula selected from the group consisting of O-glycosylated, C-glycosylated, S-glycosylated and N-glycosylated antitumor ether lipids that are useful for killing cancer stem cells in order to prevent the recurrence of tumors. In vivo the non-hydrolysable C and S-GAEL analogs will be metabolically stable and hence will have longer half-lives that will allow the attainment of therapeutic levels to kill cancer stem cells in vivo.

O-glycosides and N-glycosidic compounds in general are known to be metabolically unstable due to hydrolysis of the glycosidic bond by glycosidases in animals. Glycosidases cannot hydrolyse C- or S-glycosidic compounds. Converting O-glycosidic compounds to the C- or S-glycoside analog generates stable compounds that may retain the bioactivity. We have shown that O- and C-Gln have similar bioactivity. The C- and S-GAEL analogues are metabolically stable, meaning that therapeutic levels will be achieved in the animal to cause a significant decrease in tumor growth. It is noted that if C and S were not metabolically stable, they would not be effective in vivo. It is further of note that the N compounds included in the document are likely to be resistant to glycosidases due to the modifications around that bond.

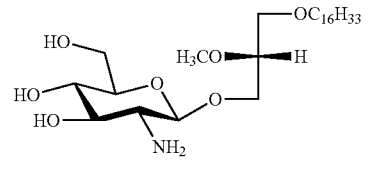

β-O-Gln

β-AO1 (R₁ = C₁₆H₃₃, Y = O; X = NH₂,
R₆ = H, R₅ = OH, R₄ = H, R₃ = OH,
R₇ = OH)

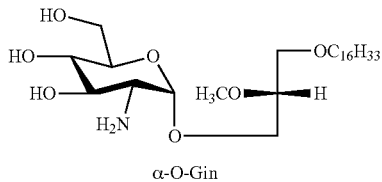

α-O-Gln

α-AO2 (R₁ = C₁₆H₃₃, Y = O; X = NH₂,
R₆ = H, R₅ = OH, R₄ = H, R₃ = OH,
R₇ = OH)

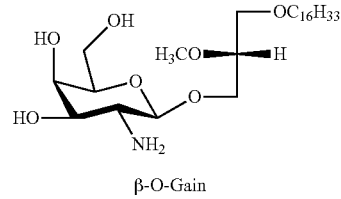

β-O-Galn

β-BO1 (R₁ = C₁₆H₃₃, Y = O; X = NH₂,
R₆ = H, R₅ = OH, R₄ = OH, R₃ = H,
R₇ = OH)

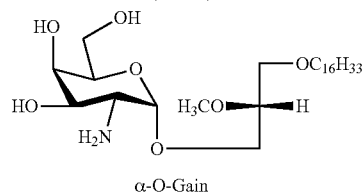

α-O-Galn

α-BO2 (R₁ = C₁₆H₃₃, Y = O; X = NH₂,
R₆ = H, R₅ = OH, R₄ = OH, R₃ = H,
R₇ = OH)

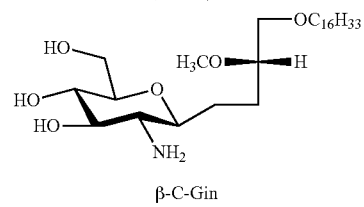

β-C-Gln

β-AC1 (R₁ = C₁₆H₃₃, Y = CH₂; X = NH₂,
R₆ = H, R₅ = OH, R₄ = H, R₃ = OH,
R₇ = OH)

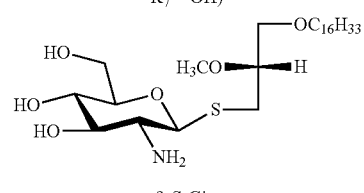

β-S-Gln

β-AS1 (R₁ = C₁₆H₃₃, Y = S; X = NH₂,
R₆ = H, R₅ = OH, R₄ = H, R₃ = OH,
R₇ = OH)

-continued

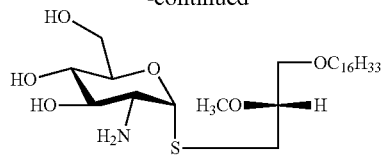

α-S-Gln

α-AS2 (R₁ = C₁₆H₃₃, Y = S; X = NH₂,
R₆ = H, R₅ = OH, R₄ = H, R₃ = OH,
R₇ = OH)

Thus according to one aspect of this invention, there is provided a method for treating or ameliorating or treating prophylactically cancers that are refractory to chemotherapeutic agents that are driven by cancer stem cells. Drug resistance is considered by many of skill in the art to be a hallmark of the cancer stem cells, meaning that all CSCs may play a role in drug resistance cancers. It is also of note that there are well defined specific markers that have been identified for cancer stem cells from different tumors. However, in general, CSC are associated with tumors that recur and/or are drug resistant.

In a further aspect of the invention, there is provided a method of treating a cancer that is refractory to treatment with existing apoptosis-inducing agents comprising administering to an individual in need of such treatment an effective amount of a GAEL as defined above.

According to a further aspect of the invention, there is provided use of any one of the above-described compounds for killing cancer stem cells and cancer stem cell spheroids.

According to another aspect of the invention, there is provided use of any one of the above-described compounds for treating a cancer that is refractory to treatment with existing apoptosis-inducing agents.

According to another aspect of the invention, there is provided the use of any one of the above-described compounds for use as a medicament for treating a cancer that is refractory to treatment with existing apoptosis-inducing agents.

According to yet another aspect of the invention, there is provided any one of the above-defined compounds for use in the treatment of cancer, for example, a cancer that is refractory to treatment with existing apoptosis-inducing agents An individual in need of such a treatment for example suffering from breast, pancreatic, ovarian, prostate, lung, head and neck, gastric, brain, liver, colon cancer, melanoma will be given an effective amount of the hydrolytic-stable active GAEL following surgery to remove the tumor mass. After a tumor is removed now the patient undergoes chemotherapy with the apoptosis inducing compounds like adriamycin, doxorubicin, taxol, taxotere, fluorouracil, cisplatin, carboplatin, cyclophosphamide, etoposide, methotrexate VP16, cytarabine (AraC), actinomycin D, and gemcitabine. They may also get radiotherapy treatment. The goal is to kill the residual cancer cells but as these likely include cancer stem cells, these treatments will not be successful unless administered a compound such as a GAEL. That is why the tumors recur.

Frequently the tumor has spread (metastasized) and surgery is not an option so chemotherapy is the primary treatment.

In one embodiment of the invention, it is envisaged that GAELs (eg α-C-Gln) may be combined with agents such as taxol, doxorubicin, gemcitabane, 5 fluorouracil or other currently used apoptosis-inducing agents to eliminate the bulk tumor cells and cancer stem cells.

The GAEL may also be given either as a stand-alone therapeutic agent, after initial treatment with an apoptosis inducing chemotherapeutic agent, or in combination therapy with an apoptosis-inducing chemotherapeutic agent. Another aspect of the invention involves providing an effective dose of GAEL to cause the shrinkage and elimination of the tumor without surgery.

Methods

Breast cancer stem cell enriched cell population was obtained by staining breast cancer cell lines BT-474 and JIMT-1 for aldehyde dehydrogenase 1 (ALDH1) using the assay kit from Stem Cell Technologies (Vancouver BC, Canada) according to the instructions of the manufacturer with the appropriate controls. BT-474 is a ductal carcinoma cell line (Lasfargues E Y, Coutinho W G, Dion A S (1979) *A human breast tumor cell line (BT-474) that supports mouse mammary tumor virus replication. In Vitro* 15, 723-729) while JIMT-1 is a carcinoma cell line that is resistant to herceptin (Tanner M, Kapanen A J, Junttila T, Raheem O, Grenman S, Elo J, Elenius K, Isola J (2004). *Characterization of a novel cell line established from a patient with herceptin-resistant breast cancer. Mol Cancer Ther* 3, 1585-1592). Following the staining, the cells stained for ALDH1 were sorted from the bulk population by flow cytometry on a 4 laser MoFloXPP high speed/pressure cell sorter. The cells were pelleted by centrifugation, resuspended in supplemented Mammocult medium (Stem Cell Technologies) and dispersed into ultra-low adhesive 6-well plates or 35 mm dishes for 7 days to allow the formation of spheroids (mammospheres). After 7 days, the spheres were separated from single cells (dead non-stem cells) by sieving the contents of the well through a 40 µM nylon cell strainer (BD Falcon). The spheres retained in the sieve are washed with Hanks buffer and subsequently trypsinised to obtain a single cell suspension of cancer stem cells. The cell numbers were determined with a Coulter ZM counter and the cells were seeded into the appropriate low adhesion tissue culture ware for various studies.

AEL solutions in ethanol were diluted into supplemented mammocult medium generally at twice the desired final concentration. A volume equal to that in the wells was added to dilute the drug to the desired concentration in each well. Subsequently any further addition of drug to the wells, utilized AEL solution prepared at the desired concentration.

Cell viability assay: Cell viability was determined by the Cell Titre 96 Aqueous One solution proliferation assay ((MTS assay; Promega) according to the instructions of the manufacturer.

Trypan blue dye exclusion assay using the TC10 automated cell counter (BioRad) was also used for some studies.

Results

ALDH1 is a stem cell marker for breast cancer stem cells and the Aldefluor assay kit from Stem Cell Technologies provides a facile method for isolating a cell fraction enriched for the cancer stem cells. BT-474 and JIMT-1 breast cancer cells were stained for ALDH1 by the aldefluor assay kit (Stem cell technologies). Cancer stem cells do not require an adhesive surface for growth and grow as tumorspheres in suspension when cultured in ultra-low adhesion tissue culture ware while the cells requiring adhesion die from anoikis (Gilmore A P (2005), *Anoikis, Cell Death Diff* 12, 1473-1477). Thus, growth of the sorted cells in these low adhesion dishes provides a mechanism to separate the stem cells from non-stem cells and further purify the material. The cells were grown in mammocult medium (Stem Cell Technologies) and large tumorspheres were formed within 7 days.

The cytotoxic effects of AELs on cancer cell lines is usually determined with cells incubated with medium containing 10% FBS. It is well established that the protein content of the incubating medium can have an impact on the effective concentrations of AELs since AELs bind to proteins in the medium. Because the mammocult medium is serum free, it was essential to see if the protein content was similar to that of 10% FBS-containing medium in order to eliminate this as the reason for any differential effects. The protein content of supplemented mammocult medium was determined to be 3 mg/ml using the BioRad assay. This value is very similar to the protein content determined for 10% FBS containing medium (Samadder P, Arthur G (1999), *Decreased sensitivity to 1-O-octadecyl-2-O-methyl glycerophosphocholine in MCF-7 cells adapted for serum-free growth correlates with constitutive association of raf-1 with cellular membranes, Cancer Res* 59, 4808-4815). Thus, any effects observed cannot be ascribed simply to the lack of protein in medium which would have effectively increased the concentration of drug available to the cells.

Figure 1A:
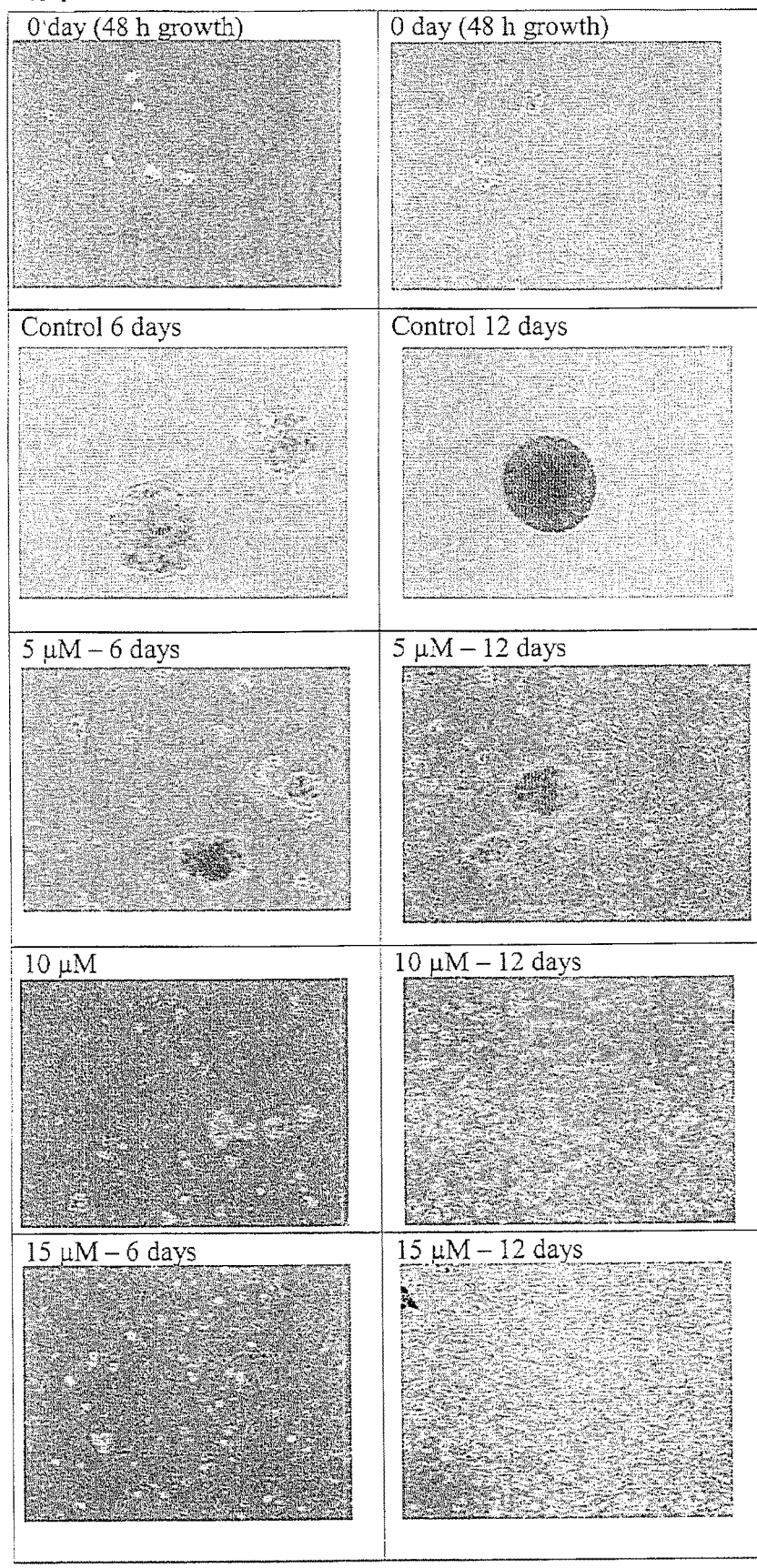
FIG. 1. A. Effect of β-C-Gln (β-AC1) on BT-474 cancer stem cell spheroid formation. BT-474 cancer stem cells were obtained by staining BT474 cells for ALDH1 and sorting the stained from unstained cells by flow cytometry. The ALDH1 stained cells were grown in ultra-low adhesion 6-well plates in mammocult medium for 7 days. The spheroids were isolated and trypsinised to generate single cells. The cells were then seeded for 2 days in ultra-low adhesion 6-well plates, and subsequently incubated in the absence or presence of C-Gln for up to 12 days. The media was replenished after 6 days. B. Effect of β-O-Gln (β-AO1), α-O-Gln (α-AO1), or ET-18-OCH$_3$ on BT-474 cancer stem cell spheroid formation.
Figure 1B:
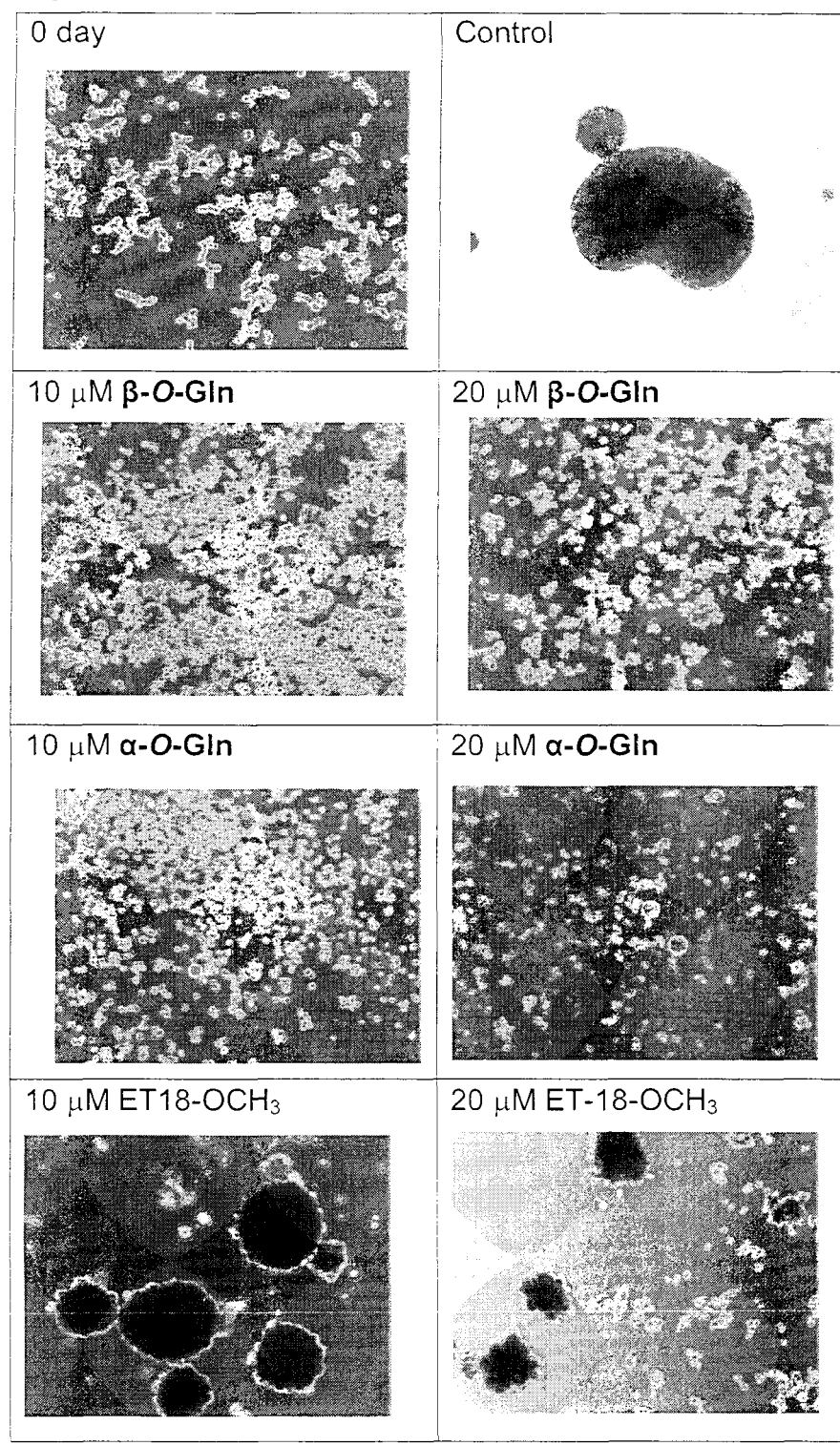
Figure 2A:
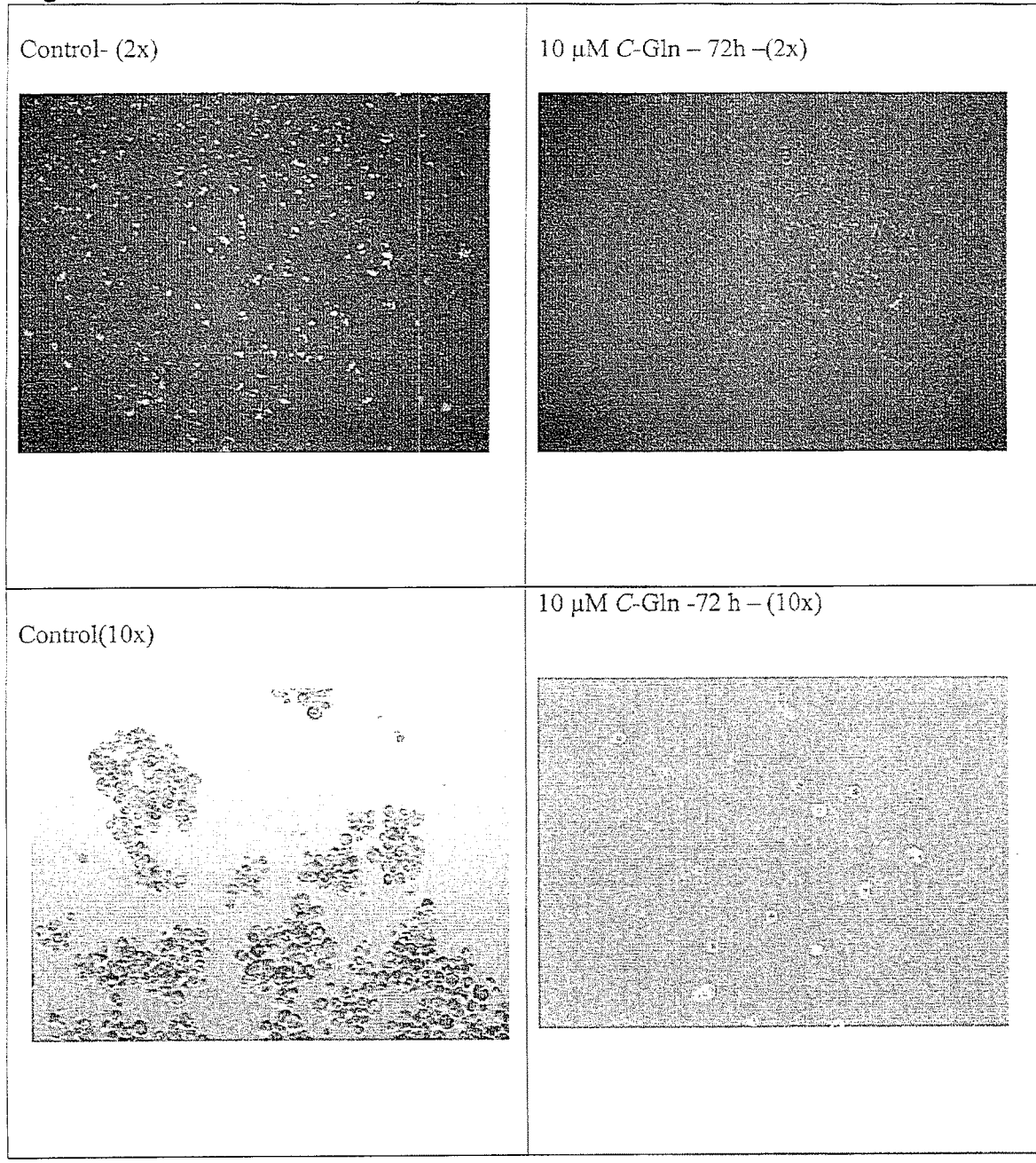
FIG. 2. A. Effect of β-C-Gln on JIMT-1 cancer stem cell spheroid formation. JIMT1 cancer stem cells were obtained by staining for ALDH1 and sorting the cells by flow cytometry. The spheroids were grown in ultra-low adhesion plates in mammocult medium. The spheroids were isolated and trypsinised to generate single cells. The cells were then seeded in the absence or presence of C-Gln in mammocult medium. Images were taken after 72 h. B. Effect of β-O-Gln, α-O-Gln, or ET-18-OCH$_3$ on BT-474 cancer stem cell spheroid formation. The experiments were conducted as described above but with different AELs. Images were taken after incubation for 6 days.
Figure 2B:
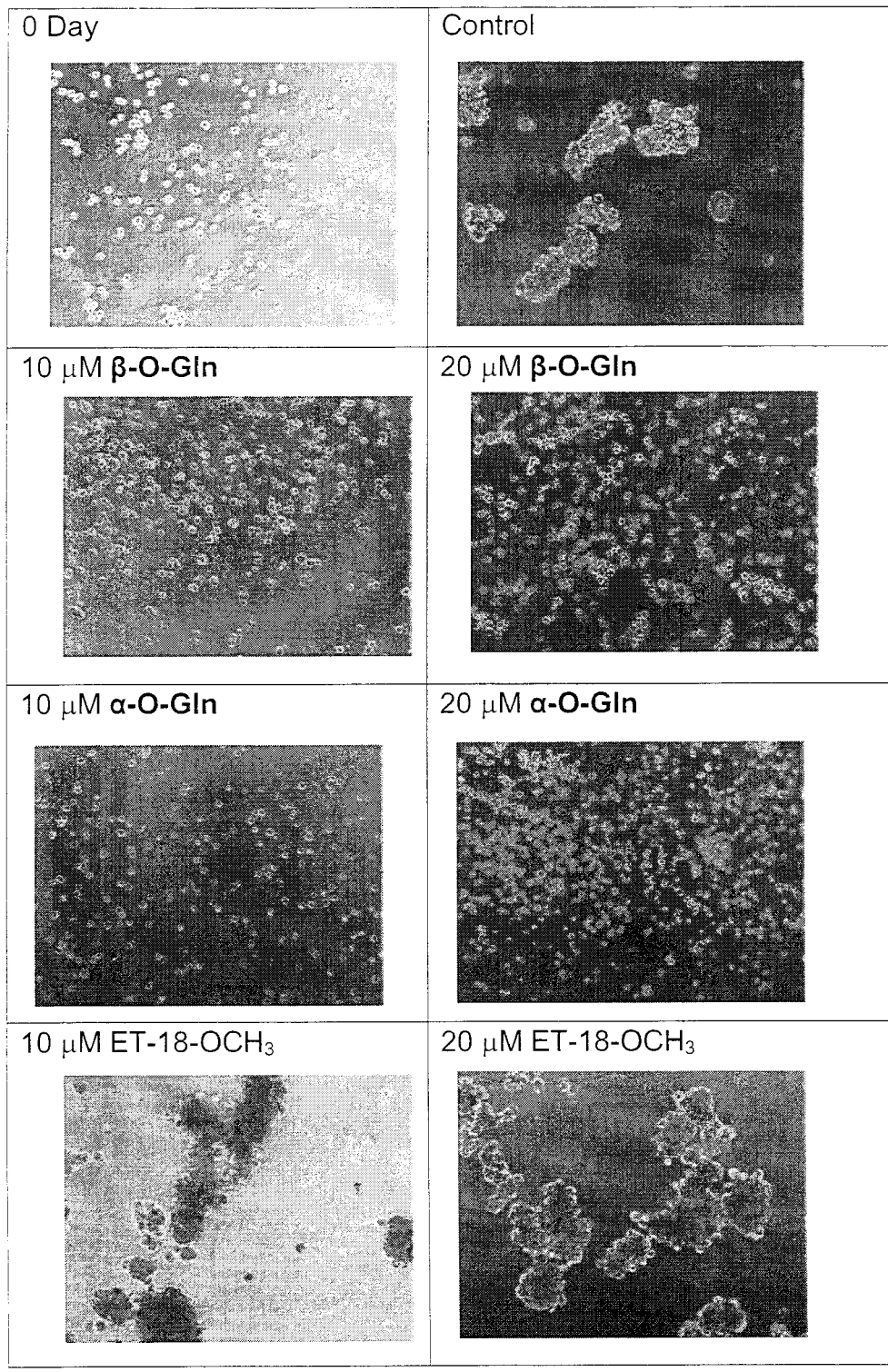

We investigated the effects of the GAELs and the ALPET-18-OCH3 on the ability of the cancer stem cells to form tumorspheres. Our studies revealed that when β-C-Gln (β-AC1), β-O-Gln (β-AO1), α-O-Gln (α-AO2), α-O-Galn (α-BO2) GAELs were added to freshly sorted cancer stem cells, at concentrations of 10 µM and above for 6 days, the cells were unable to form spheroids whereas the controls formed spheroids. The results displayed in FIG. 1A clearly show that the addition of C-Gln (β-AC1) to BT474 cancer stem cells 2 days after seeding, when spheroids have started to form, disrupted the process of spheroid formation. This was a concentration dependent event and at concentrations greater than 10 µM spheroid formation was completely disrupted. Spheroids were formed at 5 µM but these were smaller and not as compact as those formed in control incubations without GELs. The results of studies with BT474 cancer stem cells and β-O-Gln (β-AO1), α-O-Gln (α-AO2), are shown in FIG. 1B. In the presence of these compounds, the cancer stem cells were unable to form spheroids. Viability studies with trypan dye exclusion assay revealed that the cells were not viable. Similar results were obtained for α-O-Galn (α-BO2). We also performed identical studies with the "gold standard" AEL, ET-18-OCH$_3$ and the results of these studies are also displayed in FIG. 1B. Unlike the GAELs which prevented the formation of spheroids, incubation with ET-18-OCH$_3$ did not prevent spheroid formation. Similar studies with JIMT-1 breast cancer stem cells also showed that GAELs inhibited the formation of spheroids (FIGS. 2A and 2B), whereas ET-18-OCH$_3$ did not prevent spheroid formation (FIG. 2B).

Figure 3:
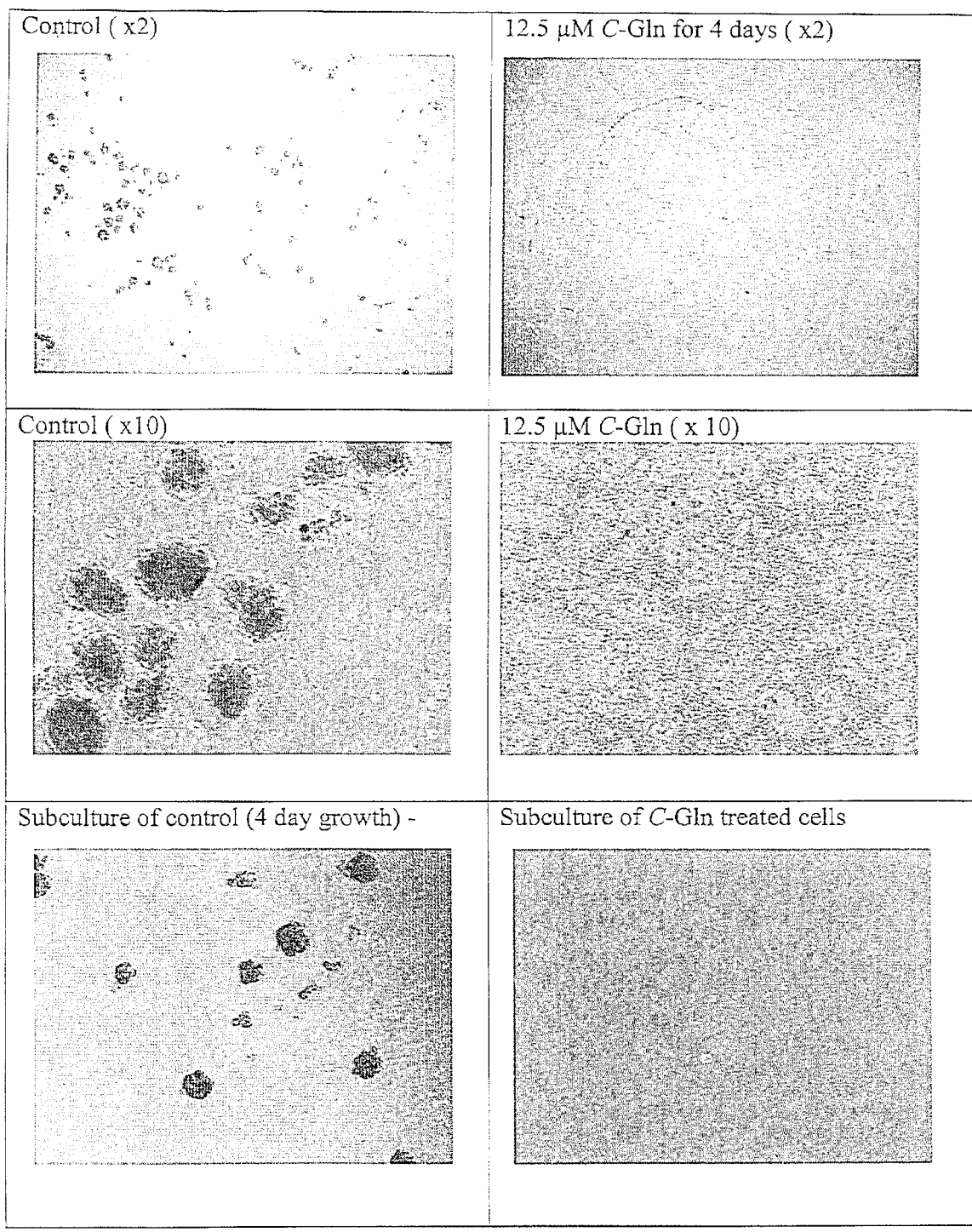
FIG. 3. Effect of β-C-Gln preincubation on subsequent growth of BT-474 cancer stem cell spheroids. BT-474 cancer stem cells were grown for 6 days in ultra low adhesion 6-well plates. The tumorspheres formed were harvested, trypsinised and cell numbers were determined. Equal numbers of cells were dispersed into 48-well non-treated plates (3-D Biotek) and grown for 4 days until moderately sized spheres were observed. The spheroids were incubated with β-C-Gln (12.5 μM) for an additional 4 days. At the end of the incubation the spheroids/cells were harvested by centrifugation and subjected to trypsinisation and subsequently cultured in mammocult growth medium without any drugs for 5 days.

Cancer stem cells grow slowly and have the ability to self renew, thus single viable cells can ultimately grow into a large mass. To confirm that the loss of viability observed as a consequence of incubating the cells with GAELs was irreversible BT-474 Cancer stem cells were grown for 4 days to form spheroids. The spheroids were incubated in the presence or absence of 12.5 µM C-Gln (β-AC1) for another 4 days. The cells were centrifuged, washed and incubated with supplemented mammocult medium without drugs. The results which are displayed in FIG. 3 shows that when the material from the cells incubated with C-Gln (β-AC1) were grown in the absence of the drug for up to 6 days, spheroids were not formed. In contrast, cells isolated from spheroids that were only incubated with the vehicle had formed spheroids. The results from these studies indicate that the loss of viability as a result of the incubation with C-Gln (β-AC1) was irreversible. The significance of these results is that GAELS can completely eradicate the cancer stem cells and hence have the potential to eliminate the chance of tumors recurring from cancer stem cells. Thus the ability of GAELs to inhibit growth of single cancer stem cells into tumorspheres is permanent beyond a certain concentration.

Figure 4A:
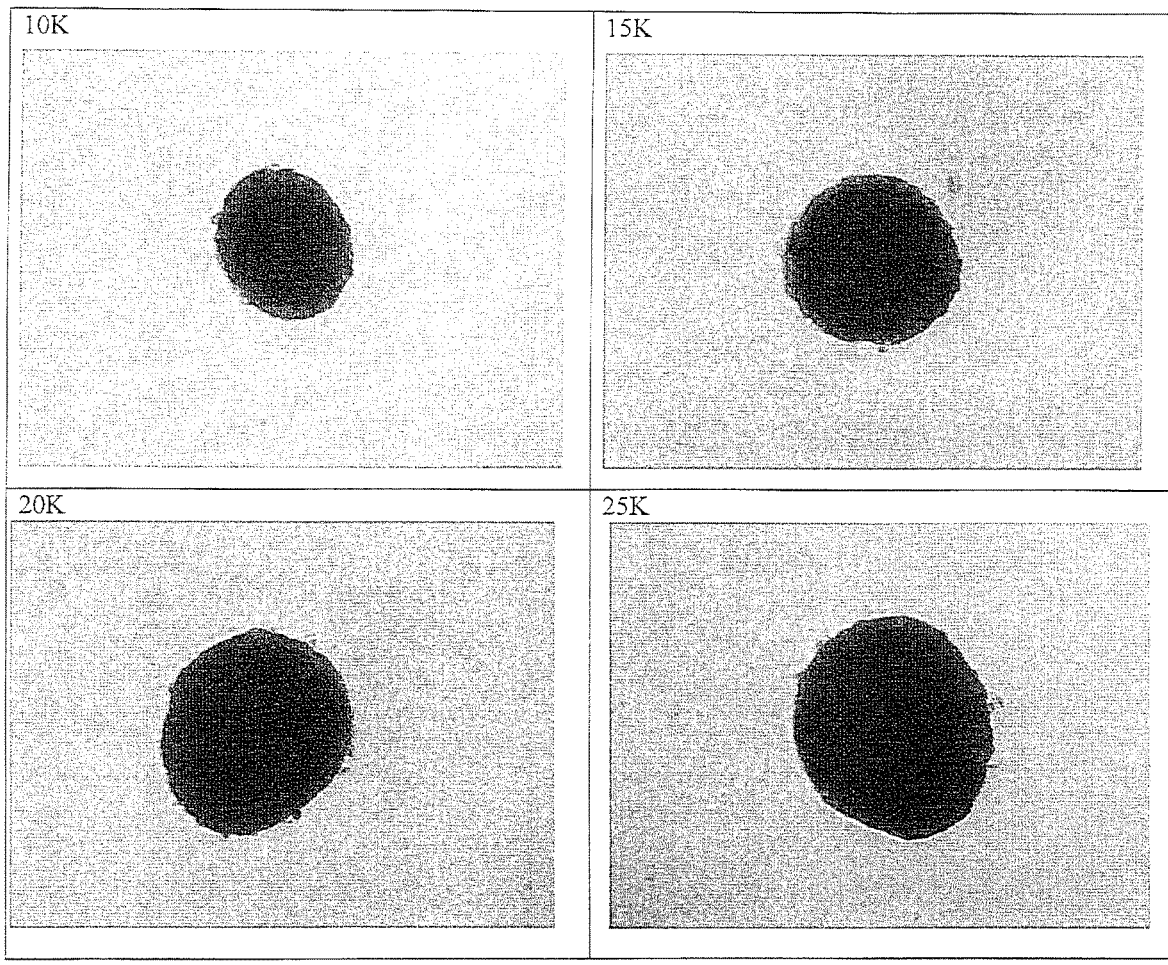
FIG. 4A. Effect of rotation on BT-474 spheroid formation. BT-474 cancer stem cells were grown for 7 days in ultra-low 6-well plates. The tumorspheres formed were harvested, trypsinised and cell numbers were determined. Different numbers of cells (10K, 15K, 20K and 25K) were dispersed into 48-well non-treated plates. The plates were rotated in a Nutating mixer in a 5% CO$_2$ incubator for 5 days.
Figure 4B:
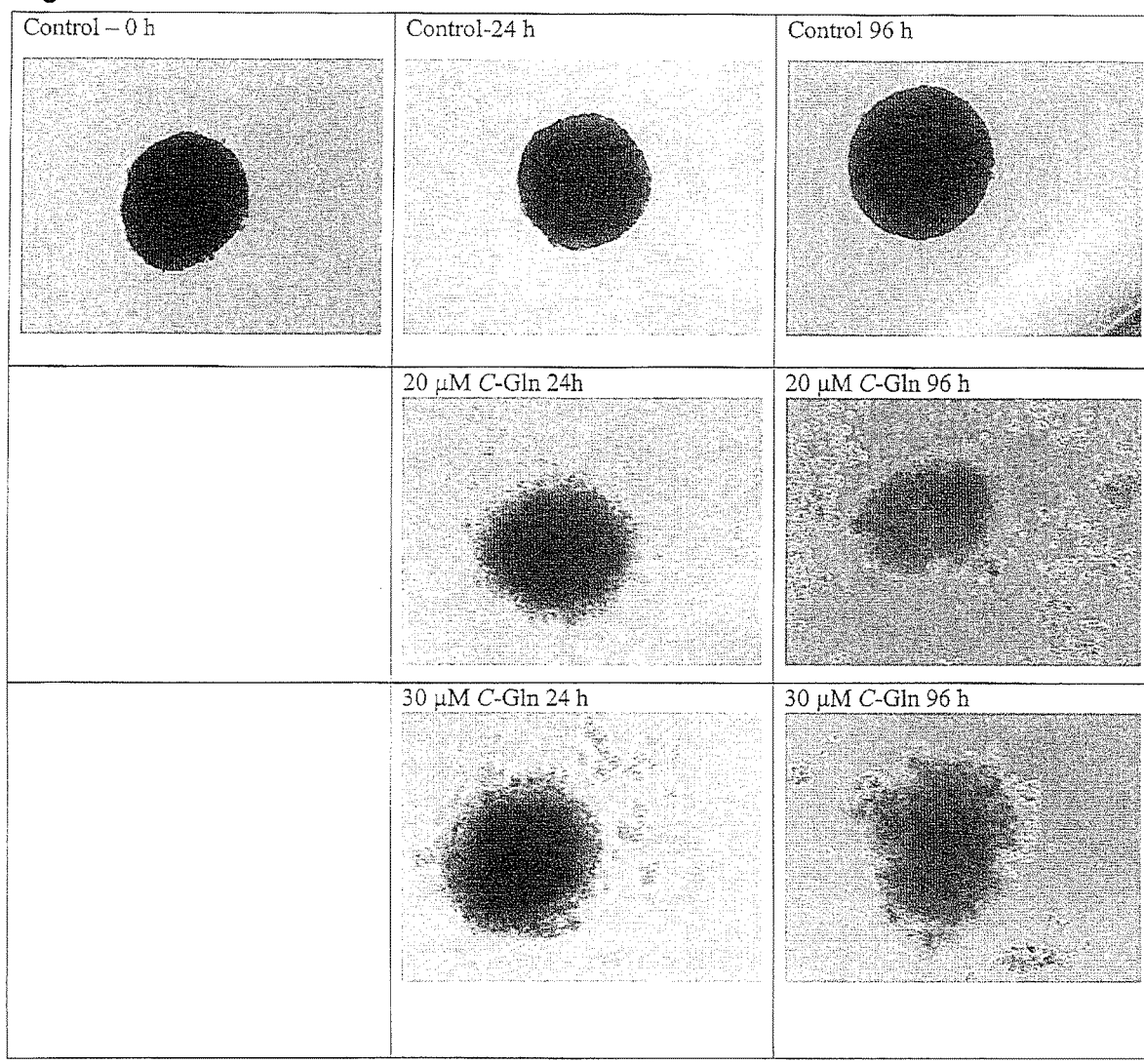
FIG. 4B. Effect of β-C-Gln on BT-474 tumorspheres formed by rotation on a nutating mixer. BT-474 spheroids obtained by rotating the plates in a nutator (see FIG. 4A), were incubated with β-C-Gln 20 or 30 μM for 96 h. Images of spheroids formed from 20000 cells were taken after 24 and 96 h.

Cancer stem cells unlike regular cancer cells are able to grow in culture in suspension and they grow by forming the spheroids. The spheroids are an aggregation of the individual cancer stem cells into a mass and as the cells divide, the mass gets bigger. Cancer stem cells are therefore grown in low adhesion plates so they do not attach. When they attach, they differentiate and lose the stem cell characteristics. On the other hand, regular cancer cells die off when they cannot adhere to the plate. In order to treat cancers, drugs have to able to kill the cells in a tumor mass. We observed that when BT-474 cells were grown under conditions of constant shaking on a Nutator mixer, the cells congregated to form a large compact sphere, the size of which was directly proportional to the number of initiating cells (FIG. 4A). These spheres were subsequently incubated with C-Gln (β-AC1) (0, 20, 30 μM) for 7 days. Within 24 h of incubation with C-Gln (β-AC1), the compact nature of the spheroid is lost, the mass is loose and single cells emanating from the mass are evident. After 96 h, the mass is very lose and amorphous and chunks of material have been lost from the main mass (FIG. 4B). After 6 days there is almost complete disintegration of the mass and when the viability of the materials in the wells were tested using the MTS assay, the cells remaining in the wells that were incubated with 20 or 30 μM C-Gln (β-AC1) were not viable (Table 1).

Figure 5A:
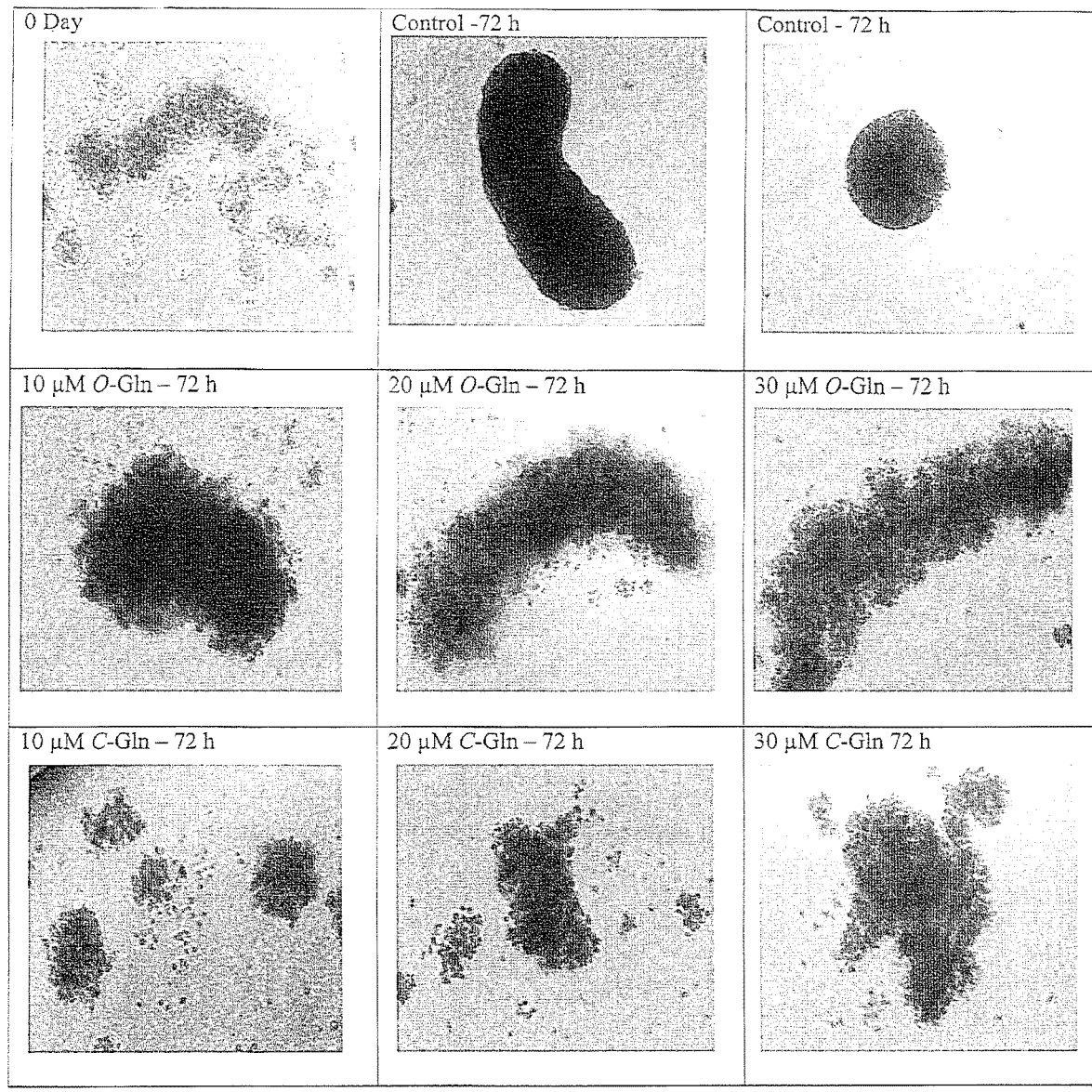
FIG. 5. A. Effect of β-O-Gln, C-Gln or ET-18-OCH$_3$ on morphology of JIMT1 stem cell spheroids. B. Effect of β-O-Gln, α-O-Gln or ET-18-OCH$_3$ on morphology of BT-474 stem cell spheroids. BT-474 cancer stem cells were grown for 7 days in ultra low adhesion 6 well plates. The tumorspheres formed were harvested, trypsinised and cell numbers were determined. Equal numbers of cells were dispersed into 48-well plates in mammocult medium and incubation was under static conditions. After spheres were formed, they were incubated with β-O-Gln, α-O-Gln or β-C-Gln (0, 10, or 30 μM) for 6 days. The medium was replenished after 3 days. Images in FIG. 5A were taken at day 0 and 72 h following addition of the compounds. Images in FIG. 5B were taken after 6 days of incubation with the compounds.
Figure 5B:
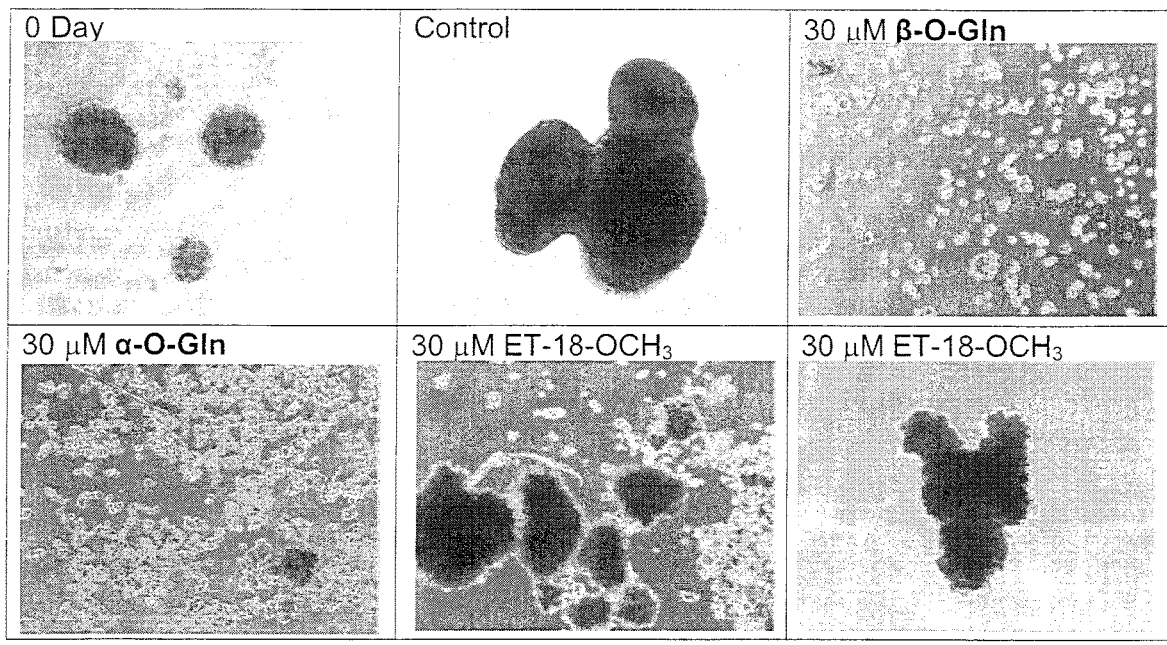

The effects of the GAELs, β-O-Gln, α-O-Gln or C-Gln on the growth and viability of tumorspheres growing under static conditions was also investigated. Studies were also conducted with ET-18-OCH$_3$ as a representative of the ALP subclass and an apoptosis inducing compound. The results for BT-474 cells are shown in FIGS. 5A and 5B. Under static conditions a large number of spheroids are formed in control incubations with the vehicle (0.1% EtOH). After 72 h treatment with β-O-Gln or β-C-Gln, there is significant disintegration of the compact spheroids observed in controls (FIG. 5A). Complete disintegration is observed after incubation with GAELs for 6 days (FIG. 5B). The results of incubations with ET-18-O—CH$_3$ are also shown in FIG. 5B. In contrast to the results obtained with GAELs, in BT-474 spheroids incubated with ET-18-OCH$_3$, relatively intact spheroids were observed even though the edges were not as compact as those found in the controls. Thus, while some disintegration had occurred it was not as comprehensive as those observed with the GAELs.

The viability of the material at the end of the incubation was determined using the MTS assay. The viability studies revealed that incubation with 10 μM of β-O-Gln, or α-O-Gln for 6 days resulted in about 60% loss of the viability of the BT-474 cells in the spheroids (FIG. 4B). In cells incubated with 10 μM of β-C-Gln, 90% of the cells were not viable. Incubation of the spheroids with 20 or 30 μM of β-O-Gln, α-O-Gln or C-Gln resulted in a total loss of viability of the cells in the spheroids. In contrast, in experiments with ET-18-OCH$_3$, 10 or 20 μM ET-18-OCH$_3$ had little effect on the viability of BT-474 spheroids and at a concentration of 30 μM viability was around 45% relative to controls. The results of the integrity studies correlate well with the viability studies.

In vitro, 30 μM is a concentration at which ET-18-OCH$_3$ kills most cancer cell lines. At that concentration, regular cancer cells will be killed and there would be no difference between the activity of GAELs and ET-18-OCH$_3$. As will be appreciated by one of skill in the art, it is the fact that it is unable to kill the stem cells even at this concentration that is significant. The reason being, ET-18-OCH$_3$ kills cells by apoptosis.

It is of note that GAELs also kill bulk tumor cells. GAELS could be used in combination with or in sequential treatment with the apoptosis inducing drugs. The apoptosis-inducing compounds would kill off the bulk tumor cells while the GAELs will be given afterwards to eradicate the cancer stem cells. And as they can be taken orally, a patient could keep taking them for a prolonged period as a prophylactic.

Figure 6:
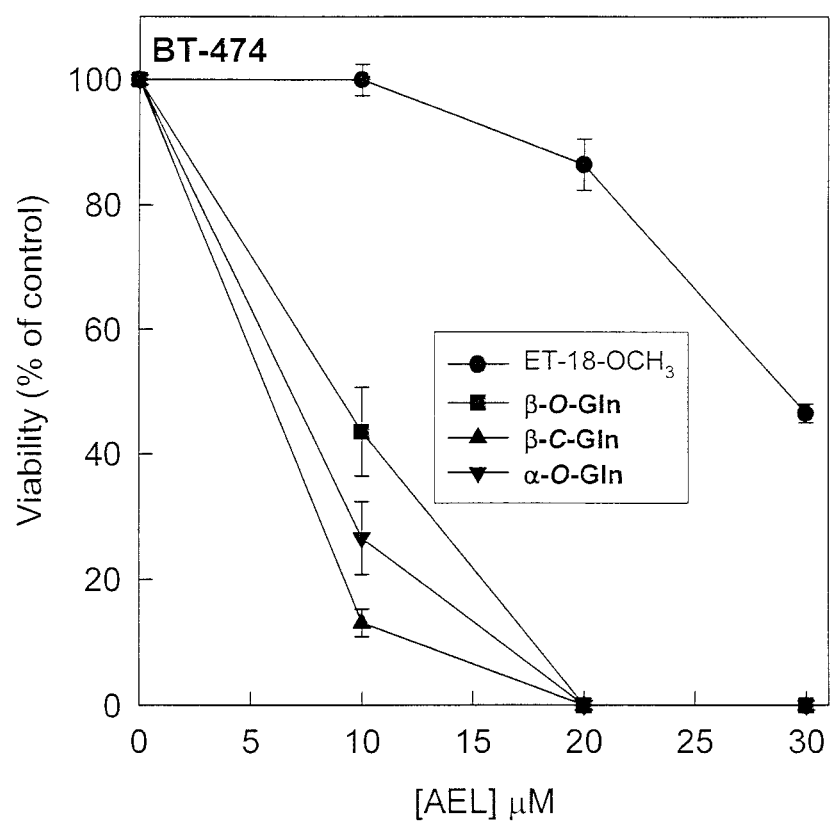
FIG. 6. Effect of β-O-Gln, α-O-Gln, β-C-Gln and ET-18-OCH$_3$ on the viability of BT-474 stem cell tumorspheres. BT-474 cancer stem cells were grown for 7 days in ultra low adhesion 6 well plates. The tumorspheres formed were harvested, trypsinised and cell numbers were determined. Equal numbers of cells were dispersed into 48-well plates in mammocult medium and incubation was under static conditions. Wells with only medium but no cells were treated in an identical manner to serve as blanks. After spheres were formed, β-O-Gln, α-O-Gln, β-C-Gln or ET-18-OCH$_3$ (0, 10, 20, 30 μM) were added and incubation was for a total of 6 days. At the end of the incubation, the MTS reagent was added to each well and the plates were rotated on a Nutator mixer in a 5% $CO_2$ incubator for 4 h. The absorbance of each well was read at 470 nm. The results are the means±standard deviation of 4 independent determinations.

The above studies were repeated with JIMT-1 spheroids. After 3 days incubation with β-O-Gln and β-C-Gln (10-30 μM) there was a profound effect on the morphology and compactness of the spheroids (FIG. 7A). As shown in FIG. 7B, 6 days following incubation with β-O-Gln or α-O-Gln, there is complete disintegration of the spheroids. In contrast, in JIMT-1 spheroids incubated with ET-18-OCH$_3$, large numbers of relatively large intact spheroids were observed along with smaller ones and some individual cells (FIG. 7B). Thus, disintegration was not as severe or complete with ET-18-OCH$_3$ as was observed with the GAELs.

Incubation of JIMT-1 tumorspheres with 10 μM of β-O-Gln or α-O-Gln resulted in 90% loss of viability of the cancer stem cells. Incubation with 10 μM β-C-Gln resulted in 65% loss of viability (FIG. 8). In contrast, incubation with 10 μM ET-18-OCH$_3$ resulted in a 40% loss of viability. Complete loss of viability was observed in cells in spheroids incubated with 20 or 30 μM of β-O-Gln, α-O-Gln or C-Gln. The viability of cells in spheroids incubated with 20 or 30 μM ET-18-OCH$_3$ was between 30-40% of controls.

We also investigated the effect of α-O-Galn, β-O-Galn or α-O-Mann on the viability of BT-474 spheroids. The spheroids were incubated with the compounds for 6 days and the viability was assessed by the MTS assay. The results obtained are displayed in Table 2. α-O-Galn was quite toxic against the cancer stem cells. Viability was down to around 10% at 10 μM concentration of the compound. Complete loss of viability was observed at concentrations of 20 or 30 μM. β-O-Galn and α-O-Mann were not as active as α-O-Galn. At a concentration of 30 μM a significant proportion (26-32%) of the BT-474 cancer stem cells were still viable. The cytotoxic efficacy of GAELs is dependent on the type of sugar moiety and the anomeric form in some instances.

Although there are a large number of chemotherapeutic agents in clinical use for cancer treatment, they have proved to have limited efficacy in the overall treatment of the disease. There is still no cure for the disease and mortality rates are still unacceptably high for most solid tumors. Evidence is accumulating that a major obstacle to preventing the recurrence of the cancer may be due to the role played by cancer stem cells (Garvalov, B. K., Acker, T. (2011) *Cancer stem cells: a new framework for the design of tumor therapies, J. Mol. Med.* 89, 95-107). These cells have been implicated in tumor progression, drug resistance and metastases and eliminating or blunting the activity of cancer stem cells is increasingly recognized to be essential towards discovering a cure for the disease (Garvalov, B. K., Acker, T. (2011) *Cancer stem cells: a new framework for the design of tumor therapies, J. Mol. Med.* 89, 95-107). Several approaches to curtail the activity of cancer stem cells in tumors have been suggested. They include direct elimination of the cancer stem cells, targeting the cancer stem cell niche to challenge their survival or reducing the aggressive behaviour of the cells by targeting the cellular machinery responsible for the behaviour. The ability of cancer stem cells to resist apoptotic cell death is one of the major reasons for the lack of efficacy of conventional drugs because these drugs invariably kill cells by apoptosis. An effective way to eliminate cancer stem cells will be to develop compounds that kill cells by non-apoptotic mechanism. Such compounds will by-pass the variety of strategies used by cancer stem cells to evade cell death by apoptosis. Since we have previously demonstrated that GAELs kill cells by a non-apoptotic mechanism that involves generation of acidic vacuoles (Samadder, P., Bittman, R., Byun, H-S, Arthur, G. (2009). *A glycosylated antitumor ether lipid kills cells by a paraptosis-like cell death. Biochem. Cell Biol.* 87, 401-414; Jahreiss, L., Renna, M., Bittman, R., Arthur, G., Rubinsztein, D. C. (2009)1-*O-hexadecyl-2-O-methyl-3-O-(2″acet-amido-2″-deoxy-β-D-glucopyranosyl)-sn-glycerol* (Gln) *induces cell death with more autophagosomes which is autophagy-independent. Autophagy* 5, 835-846), we postulated that GAELs could potentially be toxic against cancer stem cells.

Our studies have revealed that GAELs not only inhibited the growth and formation of the spheroids from the cancer stem cells isolated from BT-474 and JIMT-1 cells, but also incubation of the tumorspheres with the compounds resulted in the disintegration of the spheroids with complete loss of viability of the cells. In contrast, ET-18-OCH$_3$, the protoypic AEL which belongs to the alkyllysophospholipid subclass, did not inhibit the formation of the spheroids, and was also unable to cause the complete disintegration when incubated with preformed spheroids. Furthermore, ET-18-OCH$_3$ did not cause a total loss of viability. The differential ability of the GAELs and ET-18-OCH$_3$ to perturb cancer stem cell growth and viability is likely due to the different mode of action of these two subclasses of AELs. ET-18-OCH$_3$ kills cells by inducing apoptosis (Ruiter, G. A., Zerp, S. F., van Blitterswijk, W. J., Verheij, M. (1999) *Alkyllyso-phospholipids activate the SAPK/JNK pathway and enhance radiation induced apoptosis. Cancer Res.* 59, 2457-2463; Gajate, C., Santos-Beneit, A., Modolell, M., Moffinedo, F. (1998) *Involvement of c Jun NH2-terminal kinase activation and c-jun in the induction of apoptosis by the ether lipid 1-O-octadecyl-2-β-methyl glycerophosphocholine. Mol Pharmacol.* 53, 602-612; Smets, L. A., Van Rooij, H., Salmons, G. S. (1999). *Signaling steps in apoptosis by ether lipids. Apoptosis* 4, 419-427.) and its inability to kill all the cancer stem cells is consistent with the enhanced resistance to apoptotic cell death that has been reported as a characteristic of cancer stem cells (Hermann, P. C., Huber, S. L., Herrler, T., Aicher, A., Ellwart, J. W., Guba, M., Bruns, C. J., Heeschen, C. (2007) *Distinct populations of cancer stem cells determine tumor growth and metastatic activity in human pancreatic cancer. Cell Stem Cell* 1, 313-323; Eramo, A., Ricci-Vitiani, L., Zeuner, A., Paffini, R., Lotti, F., Sette, G., Pilozzi, E., Larocca, L. M., Peschle, C., De Maria, R. (2006) *Chemotherapy resistance of giobistoma stem cells. Cell death Differ.* 13, 1238-1241; Li, X., Lewis, M. T., Huang, J., Gutierrez, C., Osborne, C. K., Wu, M. F., Hilsenbeck, S. G., Pvlick, A., Zhang, X, Chamness, G. C., Wong, H., Rosen, J., Chang, J. C. (2008), *Intrinsic resistance of tumorigenic breast cancer cells to chemotherapy. J. Natl. Cancer. Inst.* 100, 672-679; Facompre, N., Nakagawa, H., Herlyn, M., Basu, D. (2012) *Stem-like cells and therapy resistance in squamous cell carcinomas* (2012). *Adv Parmacology* 65, 235-265.). On the other hand, the GAELs which kill cells via an apoptosis-independent mechanism were able to kill the cancer stem cells.

Without complete eradication of cancer stem cells, the cells will ultimately grow and repopulate the tumor with differentiated cells, causing the tumor to recur. An effective approach would involve the development of compounds that kill cancer stem cells via apoptosis-independent mechanisms. Such compounds acting alone or in combination with apoptosis-inducing compounds could lead to the complete elimination of the cancer stem cell population and cells of the bulk tumor which in turn would ultimately prevent the recurrence of tumors and provide the basis for a cure. The results of the studies described above have identified GAELs as compounds capable of completely eliminating cancer stem cells.

Although the hypothesis was tested with breast cancer stem cells because the basis of the activity lies in the mechanism of action, it is not a tissue specific phenomenon and is therefore expected to be applicable to all cancers.

While the preferred embodiments of the invention have been described above, it will be recognized and understood that various modifications may be made therein, and the appended claims are intended to cover all such modifications which may fall within the spirit and scope of the invention.

Synthesis of compounds α-AO2 and β-AO1, α-BO2, β-BO1, β-AC1, α-AS2 and β-AS1

Scheme 1. Synthesis of compounds α-A02 and β-AO1.

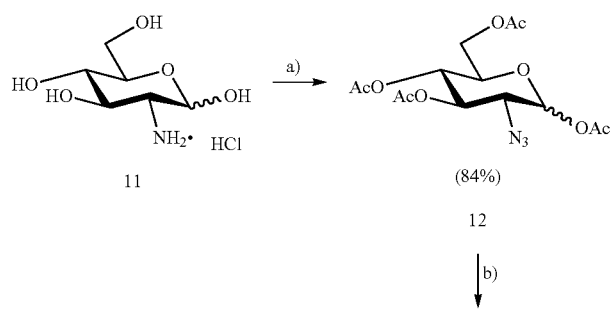

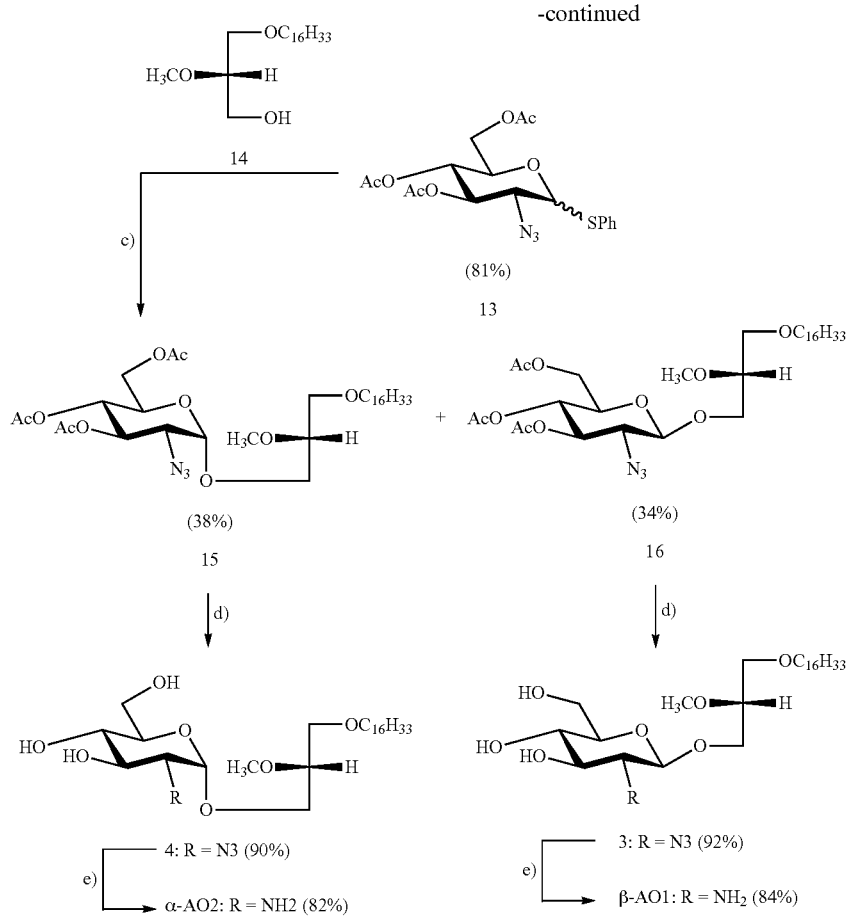

Reagents and conditions; a) (1) TfN₃, CuSO₄, Et₃N, H₂O, RT; (2) Ac₂O, DMAP, pyridine, RT; b) PhSH, BF₃/Et₂O, DCM, rt.; c) AgOTf, NIS, DCM, RT; d) NaOMe, MeOH, RT; e) Pd/C, H₂, MeOH, RT.

EXPERIMENTAL SECTION

Chemistry

Solvents were dried over $CaH_2$. $^1H$, $^{13}C$ spectra were recorded at 500 or 100 MHz, respectively and were referenced to the residual $CHCl_3$ at δ=7.24 ($^1H$) and d=77.00 ppm ($^{13}C$). TLC was carried out on Al-backed silica gel GF plates (250 mm thickness) and the compounds were visualized by charring with 10% $H_2SO_4$ in EtOH and for short wavelength UV light. The products were purified by flash chromatography on silica gel 60 (230-400 ASTM mesh) or by reverse phase C18 silica gel. HRMS and LRMS data were obtained by electrospray ionization.

Preparation of Triflic Azide Stock Solution

Sodium azide (436 mg, 6.70 mmol) was dissolved in pyridine (8.0 mL). The reaction mixture was cooled to 0° C. with vigorously stirring. Triflic anhydride (1.57 g, 5.56 mmol) was added dropwise to the mixture. The mixture was left to stir for 2 h at 0° C. to give a stock solution of triflic azide.

1,3,4,6-Tetra-O-acetyl-2-azido-2-deoxy-α/β-D-glucopyranose (12)

D-Glucosamine hydrochloride (1.00 g, 4.64 mmol) was dissolved in water (5.0 mL). Triethylamine (937 mg, 9.27 mmol) was added, along with copper sulphate pentahydrate (12 mg, 0.05 mmol). Triflic azide stock solution was then added. The blue mixture was stirred rapidly overnight, and then reduced in vacuo (water bath temperature kept below 20° C.). The resultant green syrup was dissolved in pyridine (10.0 mL), and acetic anhydride (3.0 mL) and DMAP (50 mg) were added slowly. After stirring overnight, the reaction mixture was evaporated to dryness, and the resulting residue was purified by flash chromatography (hexane/EtOAc, 3:2) to yield 12 as a yellow solid (1.44 g, 84%, predominately β☐ anomer); $R_f$ 0.13 (hexane/EtOAc, 4:1); $^1H$ NMR data were in agreement with those reported earlier.[22]

Phenyl 3,4,6-Tri-O-acetyl-2-azido-2-deoxy-1-thio-D-glucopyranoside (13)

To a solution of 12 (373 mg, 1.00 mmol) in $CH_2Cl_2$ (10 mL) at room temperature was added thiophenol (0.2 mL, 2.00 mmol) and boron trifluoride-diethyl ether (0.5 mL, 4.00 mmol). After stirring overnight, the reaction mixture was washed with saturated NaCl solution, dried with $Na_2SO_4$, and evaporated to dryness. The resulting residue was purified by flash chromatography (hexane/EtOAc, 3:1) to afforded 13 (343 mg, 81%), as a 1:3 α/β mixture; $R_f$ 0.27 (hexane/EtOAc, 3:1); $^1H$ NMR data were in agreement with those reported earlier.[32]

1-O-Hexadecyl-2-O-methyl-3-O-(2'-azido-2'-deoxy-3',4',6'-tri-O-acetyl-D-glucopyranosyl)-sn-glycerol (α anomer: 15; β anomer: 16)

To a solution of 13 (300 mg, 0.71 mmol), 14 (100 mg, 0.30 mmol), and NIS (136 mg, 0.60 mmol) in dry dichloromethane (10 mL) was added silver triflate (16 mg, 0.06 mmol). After stirring overnight, the reaction mixture was washed with saturated NaHCO$_3$ solution and water, dried over Na$_2$SO$_4$, and evaporated to dryness. The residue was purified by flash chromatography (hexane/EtOAc, 6:1), giving both 74 mg of 15 (38%) and 66 mg of 16 (34%) as a yellow solid. 15: R$_f$ 0.21 (hexane/EtOAc, 4:1); $^1$H NMR (300 MHz, CDCl$_3$): δ=5.49 (dd, J=10.6, 9.3, 1H), 5.07 (dd, J=11.5, 7.9, 2H), 4.32 (dd, J=12.3, 4.3, 1H), 4.17-4.04 (m, 2H), 3.88 (d, J=6.8, 1H), 3.67-3.53 (m, 4H), 3.52-3.40 (m, 5H), 3.30 (dd, J=10.6, 3.5, 1H), 2.16-2.01 (m, 9H), 1.59 (s, 2H), 1.27 (s, 27H), 0.90 (t, J=6.7, 3H); $^{13}$C NMR (75 MHz, CDCl$_3$): δ=170.53, 170.14, 169.58, 98.21, 79.08, 71.92, 70.27, 69.49, 68.50, 67.77, 67.57, 61.72, 60.89, 57.94, 31.79, 29.57, 29.24, 25.93, 22.55, 20.57, 14.09; EIMS: calcd for C$_{32}$H$_{57}$N$_3$Na O$_{10}^+$ 666.8. Found 666.8 [M+Na]$^+$.

16: R$_f$ 0.18 (hexane/EtOAc, 4:1); $^1$H NMR (500 MHz, CDCl$_3$): δ=5.00-4.90 (m, 2H), 4.40 (d, J=8.1, 1H), 4.22 (dd, J=12.3, 4.8, 1H), 4.07 (dd, J=12.3, 2.1, 1H), 3.96-3.89 (m, 1H), 3.73-3.66 (m, 1H), 3.66-3.58 (m, 1H), 3.56-3.36 (m, 9H), 2.05 (t, J=8.0, 6H), 1.98 (d, J=12.3, 3H), 1.55-1.48 (m, 5H), 1.21 (s, 27H), 0.84 (t, J=6.9, 3H); $^{13}$C NMR (126 MHz, CDCl$_3$): δ=170.59, 169.95, 169.59, 102.19, 79.01, 72.42, 71.82, 69.63, 69.36, 68.43, 63.80, 61.91, 57.98, 31.91, 29.69, 29.64, 29.61, 29.48, 29.35, 26.10, 22.68, 20.70, 20.67, 20.57, 14.10; EIMS: calcd for C$_{32}$H$_{57}$N$_3$Na O$_{10}^+$ 666.8. Found 666.8 [M+Na]$^+$.

1-O-Hexadecyl-2-O-methyl-3-O-(2'-azido-2'-deoxy-D-glucopyranosyl)-sn-glycerol (α anomer 3; β anomer: 4)

To a solution of 15 (74 mg, 0.11 mmol) in MeOH (5 mL) at room temperature was added NaOMe until pH came up to 9. The reaction mixture was stirred overnight, neutralized with Amberlite IR120 H$^+$ exchange resin, filtered, and evaporated under vacuum to afford a yellow solid. The residue was purified by flash chromatography (DCM/MeOH, 10:1) to afford 4 (52 mg, 90%) as a yellow solid; R$_f$ 0.26 (DCM/MeOH, 10:1); [α]$^{25}_D$ 62.4° (c 0.1, MeOH); $^1$H NMR (300 MHz, CD$_3$OD): δ=4.97 (d, 1H, J=3.4, H-1), 4.09-3.97 (m, 1H), 3.91-3.80 (m, 3H), 3.77-3.68 (m, 1H, H-2), 3.68-3.52 (m, 5H), 3.51-3.42 (m, 5H), 3.19 (dd, J=10.3, 3.4, 1H), 1.64-1.52 (m, 2H), 1.27 (s, 28H, OCH$_2$CH$_2$(CH$_2$)$_{13}$CH$_3$), 0.90 (t, J=6.7, 3H, CH$_2$CH$_3$); $^{13}$C NMR (75 MHz, CDCl$_3$): δ=98.5 (C-1), 79.3 (C-2), 71.9, 71.5, 71.3, 70.5, 69.7, 67.3, 62.8, 61.4, 57.9, 31.9, 29.7, 29.7, 29.6, 29.5, 29.4, 26.1, 22.7, 14.1 (CH$_2$CH$_3$); ESI-HRMS: calcd for C$_{26}$H$_{51}$N$_3$O$_7$Na$^+$ 540.3625. Found 540.3602 [M+M]$^+$.

49 mg of 3 (92%) was obtained from 66 mg of 16 (0.10 mmol) according to above procedure; R$_f$ 0.23 (DCM/MeOH, 10:1); [α]$^{25}_D$ 82.1° (c 0.1, MeOH); $^1$H NMR (500 MHz, CD$_3$OD): δ=4.40 (d, 1H, J=7.5, H-1), 4.24 (s, 1H), 4.11 (s, 1H, H-2), 3.97 (dd, J=10.4, 5.7, 1H), 3.88 (s, 2H), 3.71 (dd, J=10.4, 4.3, 1H), 3.64-3.52 (m, 4H), 3.51-3.41 (m, 6H), 1.64-1.53 (m, 2H), 1.27 (s, 29H, OCH$_2$CH$_2$(CH$_2$)$_{13}$CH$_3$), 0.89 (t, J=6.7, 3H, CH$_2$CH$_3$); $^{13}$C NMR (75 MHz, CDCl$_3$): δ=102.4 (C-1), 79.2 (C-2), 77.5, 77.0, 76.6, 75.4, 74.8, 71.9, 70.0, 69.7, 69.6, 65.9, 61.7, 58.1, 31.9, 29.7, 29.7, 29.6, 29.5, 29.4, 26.1, 22.7, 14.1 (CH$_2$CH$_3$); ESI-HRMS: calcd for C$_{26}$H$_{51}$N$_3$O$_7$Na$^+$ 540.3625. Found 540.3634 [M+Na]$^+$.

1-O-Hexadecyl-2-O-methyl-3-O-(2'-amino-2'-deoxy-D-glucopyranosyl)-sn-glycerol α-AO2; β anomer: β-AO1

To a solution of 3 (49 mg, 0.09 mmol) in MeOH (5 mL) at room temperature was added 10 wt % of Pd/C (10 mg). The mixture was stirred under the atmosphere of hydrogen for 2 h, filtered, and then evaporated to dryness. The resulting residue was purified by flash chromatography (DCM/MeOH, 6:1) to afford β-AO1 as a white solid (39 mg, 84%); R$_f$ 0.15 (DCM/MeOH, 6:1); [α]$^{25}_D$−20.3° (c 0.1, MeOH); $^1$H NMR (500 MHz, CD$_3$OD): δ=4.25 (d, 1H, J=8.0, H-1), 3.93 (dd, J=10.7, 4.6, 1H), 3.85 (d, J=11.8, 1H), 3.66 (dd, J=10.6, 3.9, 2H), 3.60-3.53 (m, 2H), 3.53-3.41 (m, 7H), 3.26-3.21 (m, 2H), 2.59 (t, 1H, J=15.1, H-2), 1.54 (dd, J=13.7, 6.7, 2H), 1.27 (s, 29H, OCH$_2$CH$_2$(CH$_2$)$_{13}$CH$_3$), 0.88 (t, J=6.9, 3H, CH$_2$CH$_3$); $^{13}$C NMR (126 MHz, CD$_3$OD): δ=104.31 (C-1), 80.56, 78.27, 77.20, 72.66, 71.81, 71.42, 69.66, 62.73 (C-2), 58.24, 58.13, 33.07, 30.77, 30.73, 30.59, 30.47, 27.23, 23.73, 14.43 (CH$_2$CH$_3$); ESI-HRMS: calcd for C$_{26}$H$_{53}$NO$_7$Na$^+$ 514.3720. Found 514.3706 [M+Na]$^+$. 40 mg of α-AO2 (82%) was obtained from 52 mg of 4 (0.10 mmol) according to above procedure; R$_f$ 0.13 (DCM/MeOH, 6:1); [α]$^{25}_D$ 15.7° (c 0.1, MeOH); $^1$H NMR (300 MHz, CD$_3$OD): δ=4.83 (d, 1H, J=3.2, H-1), 3.93-3.78 (m, 2H), 3.72 (dd, J=11.7, 5.2, 1H), 3.64-3.43 (m, 11H), 3.38 (s, 1H), 2.64 (dd, 1H, J=9.9, 3.4, H-2), 1.58 (d, J=6.4, 2H), 1.43-1.23 (m, 27H, OCH$_2$CH$_2$(CH$_2$)$_{13}$CH$_3$), 0.97-0.85 (m, 3H, CH$_2$CH$_3$); $^{13}$C NMR (75 MHz, CD$_3$OD): δ=100.56 (C-1), 80.59, 75.99, 74.25, 72.72, 71.89, 71.23, 68.10, 62.66 (C-2), 58.08, 57.18, 33.09, 30.80, 30.62, 30.49, 27.27, 23.75, 14.45 (CH$_2$CH$_3$); ESI-HRMS: calcd for C$_{26}$H$_{53}$NO$_7$Na$^+$ 514.3720. Found 514.3741 [M+Na]$^+$.

Synthesis of compounds α-BO2 and β-BO1

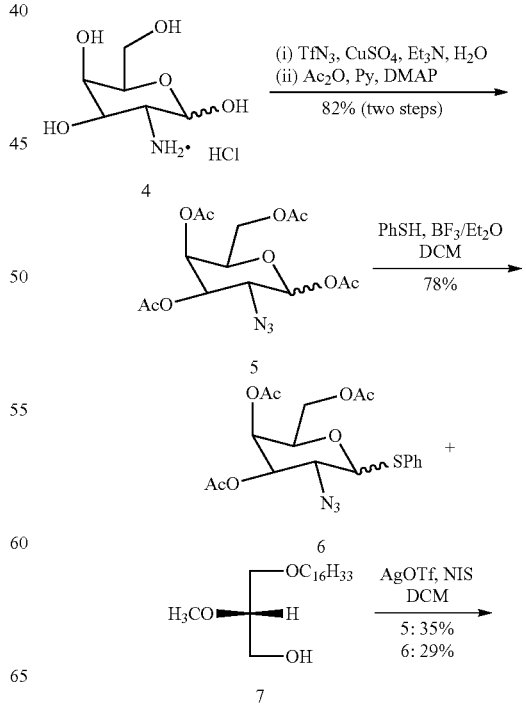

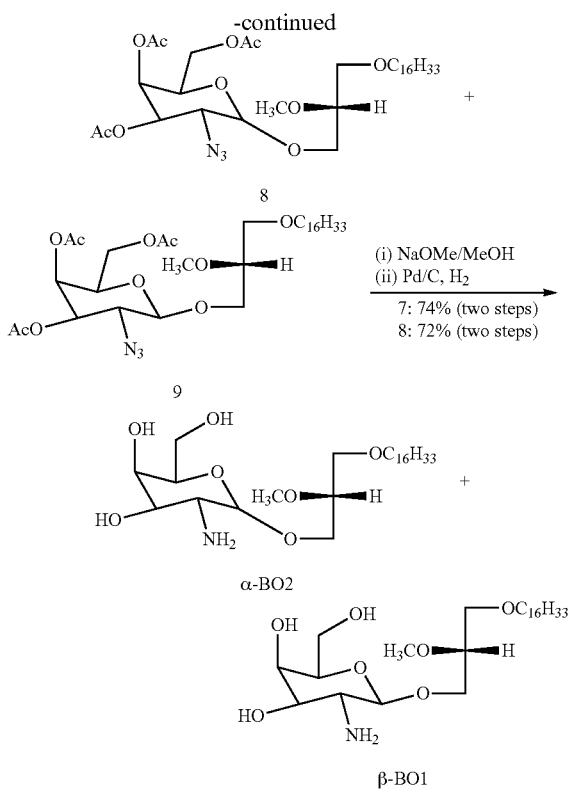

1,3,4,6-Tetra-O-acetyl-2-azido-2-deoxy-α/β-D-galactopyranose (5)

D-Galactosamine hydrochloride (1.00 g, 4.64 mmol) was dissolved in water (5.0 mL). Triethylamine (937 mg, 9.27 mmol) was added, along with copper sulphate pentahydrate (12 mg, 0.05 mmol). Triflic azide stock solution was then added. The blue mixture was stirred rapidly overnight, and then reduced in vacuo (water bath temperature kept below 20° C.). The resultant green syrup was dissolved in pyridine (10.0 mL), and acetic anhydride (3.0 mL) and DMAP (50 mg) were added slowly. After stirring overnight, the reaction mixture was evaporated to dryness, and the resulting residue was purified by flash chromatography (hexane/EtOAc, 3:2) to yield 5 as a yellow solid (1.41 g, 82%, a 3:2 α/β mixture); $R_f$ 0.12 (hexane/EtOAc, 4:1); $^1$H NMR data were in agreement with those reported earlier.[1]

Phenyl 3,4,6-Tri-O-acetyl-2-azido-2-deoxy-1-thio-D-galactopyranoside (6)

To a solution of 5 (373 mg, 1.00 mmol) in $CH_2Cl_2$ (10 mL) at room temperature was added thiophenol (0.2 mL, 2.00 mmol) and boron trifluoride-diethyl ether (0.5 mL, 4.00 mmol). After stirring overnight, the reaction mixture was washed with saturated NaCl solution, dried with $Na_2SO_4$, and evaporated to dryness. The resulting residue was purified by flash chromatography (hexane/EtOAc, 3:1) to afforded 6 (330 mg, 78%), as a 1:3 α/β mixture; $R_f$ 0.25 (hexane/EtOAc, 3:1); $^1$H NMR data were in agreement with those reported earlier.[2]

1-O-Hexadecyl-2-O-methyl-3-O-(2'-azido-2'-deoxy-3',4',6'-tri-O-acetyl-D-galactopyranosyl)-sn-glycerol (α anomer: 8; β anomer: 9)

To a solution of 6 (300 mg, 0.71 mmol), 7 (100 mg, 0.30 mmol), and NIS (136 mg, 0.60 mmol) in dry dichloromethane (10 mL) was added silver triflate (16 mg, 0.06 mmol). After stirring overnight, the reaction mixture was washed with saturated $NaHCO_3$ solution and water, dried over $Na_2SO_4$, and evaporated to dryness. The residue was purified by flash chromatography (hexane/EtOAc, 6:1), giving both 68 mg of 8 (35%) and 56 mg of 9 (29%) as a yellow solid.

8: $R_f$ 0.20 (hexane/EtOAc, 4:1); $^1$H NMR (300 MHz, $CDCl_3$): δ=5.47 (d, J=2.2, 1H), 5.38 (dd, J=11.1, 3.3, 1H), 5.07 (d, J=3.5, 1H), 4.30 (t, J=6.6, 1H), 4.15-4.07 (m, 2H), 3.92-3.83 (m, 1H), 3.67-3.60 (m, 2H), 3.58-3.52 (m, 3H), 3.50-3.43 (m, 5H), 2.16 (s, 3H), 2.07 (d, J=4.3, 6H), 1.58 (d, J=9.1, 2H), 1.27 (s, 27H), 0.90 (t, J=6.7, 3H); $^{13}$C NMR (75 MHz, $CDCl_3$): δ=170.34, 170.06, 169.82, 98.47, 79.10, 71.89, 69.62, 68.06, 67.92, 67.64, 66.63, 61.62, 57.97, 57.49, 31.94, 29.71, 29.67, 29.65, 29.51, 29.37, 26.10, 22.70, 20.67, 20.63, 14.12; EIMS: calcd for $C_{32}H_{57}N_3Na\,O_{10}^+$ 666.8. Found 666.9 $[M+Na]^+$.

9: $R_f$ 0.17 (hexane/EtOAc, 4:1); $^1$H NMR (300 MHz, $CDCl_3$): δ=5.34 (d, J=2.6, 1H), 4.79 (dt, J=10.9, 4.1, 1H), 4.42 (d, J=8.0, 1H), 4.22-4.10 (m, 2H), 4.03-3.96 (m, 1H), 3.87 (dt, J=6.7, 3.3, 1H), 3.78-3.65 (m, 2H), 3.62-3.55 (m, 3H), 3.51-3.43 (m, 5H), 2.20-2.13 (m, 3H), 2.08 (dd, J=9.8, 5.0, 6H), 1.58 (dd, J=14.3, 7.4, 2H), 1.27 (s, 26H), 0.89 (t, J=6.7, 3H); $^{13}$C NMR (75 MHz, $CDCl_3$): δ=170.35, 170.07, 169.80, 102.57, 79.08, 71.84, 70.98, 70.73, 69.73, 69.36, 66.38, 61.23, 60.98, 58.02, 31.93, 29.71, 29.66, 29.63, 29.51, 29.37, 26.13, 22.70, 20.66, 20.62, 14.12; EIMS: calcd for $C_{32}H_{57}N_3Na\,O_{10}^+$ 666.8. Found 666.8 $[M+Na]^+$.

1-O-Hexadecyl-2-O-methyl-3-O-(2'-amino-2'-deoxy-D-galactopyranosyl)-sn-glycerol (α anomer: α-BO2; β anomer: β-BO1 2)

To a solution of 8 (68 mg, 0.11 mmol) in MeOH (5 mL) at room temperature was added NaOMe until pH came up to 9. The reaction mixture was stirred overnight, neutralized with Amberlite IR120 $H^+$ exchange resin, filtered, and then added by 10 wt % of Pd/C (10 mg). The mixture was stirred under the atmosphere of hydrogen for 2 h, filtered, and then evaporated to dryness. The resulting residue was purified by flash chromatography (DCM/MeOH, 6:1) to afford α-BO2 as a white solid (38 mg, 74%); $R_f$ 0.14 (DCM/MeOH, 6:1); $^1$HNMR (500 MHz, $CD_3OD$): δ=3.87-3.76 (m, 3H), 3.69 (p, J=11.2, 2H), 3.55 (d, J=8.3, 3H), 3.51-3.43 (m, 7H), 3.29 (s, 1H), 2.98-2.90 (m, 1H), 1.54 (d, J=6.4, 2H), 1.27 (s, 31H), 0.88 (t, J=6.5, 3H); $^{13}$C NMR (126 MHz, $CD_3OD$): δ=100.95, 98.77, 80.60, 72.85, 72.69, 72.67, 72.36, 71.37, 71.21, 70.37, 68.14, 62.85, 58.10, 52.72, 33.09, 30.80, 30.77, 30.62, 30.49, 27.26, 23.75, 14.47; ESI-HRMS: calcd for $C_{26}H_{53}NO_7Na^+$ 514.3720. Found 514.3726 $[M+Na]^+$.

31 mg of β-BO1 (72%) was obtained from 56 mg of 9 (0.10 mmol) according to above procedure; $R_f$ 0.12 (DCM/MeOH, 6:1); $^1$H NMR (500 MHz, $CD_3OD$): δ=4.20 (d, J=8.0, 1H), 3.93 (dd, J=10.7, 4.5, 1H), 3.78-3.64 (m, 4H), 3.56 (d, J=7.3, 2H), 3.50 (dd, J=11.5, 6.9, 2H), 3.47-3.42 (m, 5H), 3.40 (dd, J=10.0, 2.9, 1H), 2.92 (dd, J=10.2, 8.2, 1H), 1.54 (dd, J=13.9, 6.7, 2H), 1.29 (d, J=17.5, 28H), 0.88 (t, J=6.9, 3H); $^{13}$C NMR (126 MHz, $CD_3OD$): δ=104.83, 80.57, 76.98, 74.24, 72.66, 71.47, 69.56, 69.47, 62.52, 58.11, 54.66, 33.07, 30.77, 30.74, 30.59, 30.46, 27.23, 23.72, 14.42; ESI-HRMS: calcd for $C_{26}H_{53}NO_7Na^+$ 514.3720. Found 514.3713 $[M+Na]^+$.

β-BC1 was prepared according to previously published procedure Yang, Guangli; Franck, Richard W.; Bittman, Robert; Samadder, Pranati; Arthur, Gilbert Organic Letters (2001), 3(2), 197-200.

Synthesis of compounds α-AS2 and β-AS1

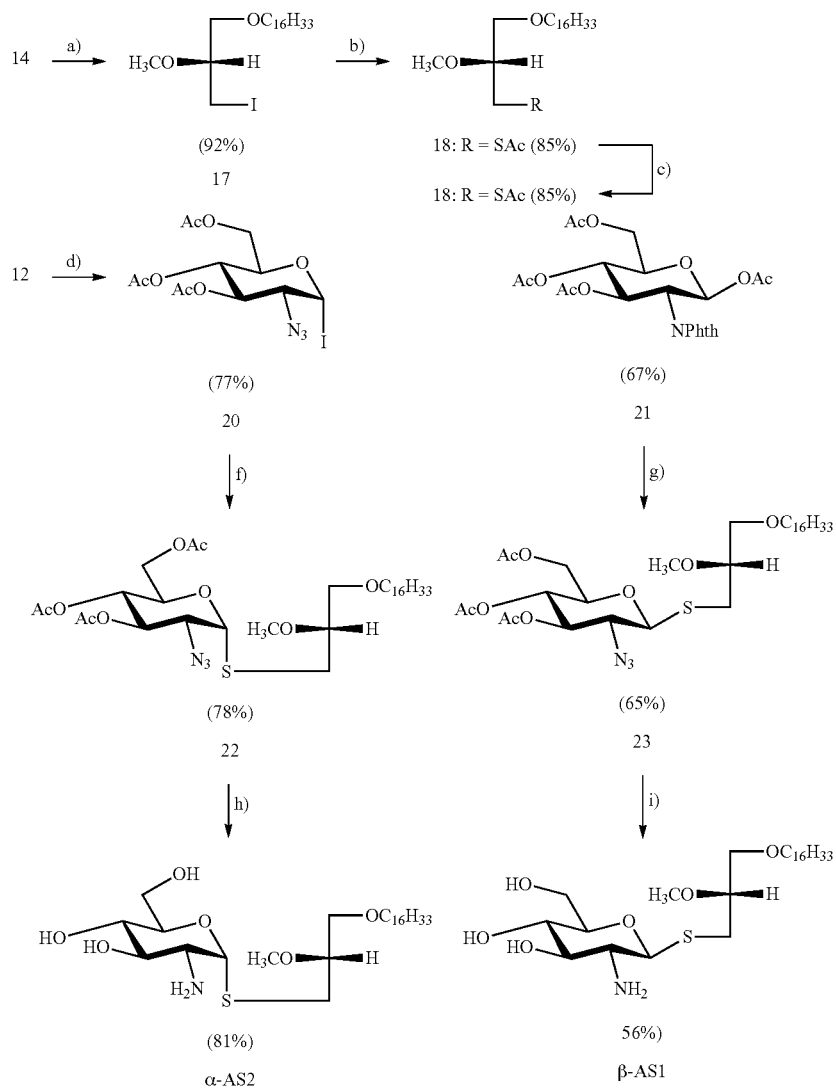

Scheme 2 Synthesis of compounds α-AS2 amd β-AS1 and 9.

Reagents and conditions: a) PPh₃, I₂, imidazole, toluene, reflux; b) AcSK, acetone, RT; c) NaOMe, MeOH, RT; d) aluminium metal, I₂, DCM, RT; e) (1) 1M NaOH, phthalic anhydride, rt; (2) Ac₂O, DMAP, pyridine, RT; f) AgOTf, DCM, RT; g) BF₃/Et₂O, DCM, RT; h) (1) NaOMe, MeOH, RT; (2) Pd/C, H₂, MeOH, RT; i) MeNH₂/EtOH, reflux.

1-O-Hexadecyl-2-O-methyl-3-iodide-sn-glycerol (17)

To a solution of 14 (660 mg, 2.00 mmol) in toluene (10 mL) at room temperature was added PPh₃ (524 mg, 2.00 mmol), I₂ (508 mg, 2.00 mmol) and imizadole (272 mg, 4.00 mmol). The reaction mixture was heated to reflux and stirred overnight, and then evaporated to dryness. The resulting residue was purified by flash chromatography (hexane/EtOAc, 6:1) to afford 17 as a yellow solid (810 mg, 92%); $R_f$ 0.28 (hexane/EtOAc, 6:1); $^1$H NMR (300 MHz, CDCl₃): δ=3.58 (dd, J=10.0, 4.8, 1H), 3.54-3.43 (m, 6H), 3.42-3.32 (m, 2H), 3.31-3.24 (m, 1H), 1.57 (dd, J=14.0, 7.2, 2H), 1.27 (s, 27H), 0.90 (t, J=6.7, 3H).

1-O-Hexadecyl-2-O-methyl-3-S-acetyl-sn-glycerol (18)

To a solution of 17 (660 mg, 1.50 mmol) in acetone (10 mL) at room temperature was added AcSK (343 mg, 3.00 mmol). After stirring overnight, the mixture was evaporated to dryness. The resulting residue was purified by flash chromatography (hexane/EtOAc, 5:1) to afford 18 as a yellow solid (496 mg, 85%); $R_f$ 0.26 (hexane/EtOAc, 5:1); $^1$H NMR (300 MHz, CDCl₃): δ=3.51-3.42 (m, 8H), 3.17-3.08 (m, 2H), 2.36 (s, 3H), 1.65-1.52 (m, 2H), 1.27 (s, 28H), 0.89 (t, J=6.7, 3H).

1-O-Hexadecyl-2-O-methyl-3-thiol-sn-glycerol (19)

To a solution of 18 (480 mg, 1.23 mmol) in MeOH (10 mL) at room temperature was added NaOMe until pH came up to 9. The mixture was stirred overnight, neutralized with Amberlite IR120H$^+$ exchange resin, filtered, and evaporated to dryness. The resulting residue was purified by flash chromatography (hexane/EtOAc, 6:1) to afford 19 as a yellow solid (239 mg, 56%); R$_f$ 0.24 (hexane/EtOAc, 6:1); $^1$H NMR (300 MHz, CDCl$_3$): δ=3.63-3.28 (m, 8H), 2.85-2.59 (m, 21-1), 1.86-1.47 (m, 2H), 1.27 (s, 26H), 0.97 (dt, J=13.4, 6.7, 3H).

3,4,6-Tri-O-acetyl-2-azido-2-deoxy-α-D-glucopyranosyl iodide (20)

To a solution of 12 (200 mg, 0.54 mmol) in DCM (10 mL) at room temperature was added Aluminum metal (10 mg) and iodide (40 mg). The mixture was stirred overnight, and evaporated to dryness. The resulting residue was purified by flash chromatography (hexane/EtOAc, 4:1) to afford 20 as a yellow solid (182 mg, 77%); R$_f$ 0.22 (hexane/EtOAc, 4:1); $^1$H NMR data were in agreement with those reported earlier.[24]

1-O-Hexadecyl-2-O-methyl-3-S-(2'-azido-2'-deoxy-3',4',6'-tri-O-acetyl-α-D-glucopyranosyl)-sn-glycerol (22)

To a solution of 19 (100 mg, 0.29 mmol) and 20 (127 mg, 0.29 mmol) was added a suspension of silver triflate (34 mg, 0.14 mmol) in dry dichloromethane (10 mL). After stirring overnight, the reaction mixture was washed with saturated NaHCO$_3$ solution and water, dried over Na$_2$SO$_4$, and concentrated under reduced pressure. The residue was purified by flash chromatography (hexane/EtOAc, 6:1) to afford 22 (149 mg, 78%) of as a yellow solid; R$_f$ 0.21 (hexane/EtOAc, 6:1); $^1$H NMR (300 MHz, CDCl$_3$): δ=5.56 (d, J=5.6, 1H), 5.30 (dd, J=10.3, 9.4, 1H), 5.10-4.98 (m, 1H), 4.46 (ddd, J=10.1, 4.5, 2.1, 1H), 4.33 (dd, J=12.3, 4.6, 1H), 4.05 (ddd, J=16.1, 11.4, 3.9, 2H), 3.60-3.38 (m, 8H), 2.82-2.72 (m, 2H), 2.12-2.02 (m, 9H), 1.62-1.52 (m, 2H), 1.27 (s, 30H), 0.89 (t, J=6.7, 3H); $^{13}$C NMR (75 MHz, CDCl$_3$): δ=170.53, 169.79, 83.47, 80.17, 71.97, 71.85, 71.06, 68.73, 68.01, 61.93, 61.57, 57.93, 31.93, 31.09, 29.71, 29.67, 29.65, 29.62, 29.49, 29.37, 26.11, 22.70, 20.69, 20.66, 20.60, 14.12; EIMS: calcd for C$_{32}$H$_{57}$N$_3$O$_9$SNa$^+$ 682.9. Found 682.5 [M+Na]$^+$.

1-O-Hexadecyl-2-O-methyl-3-S-(2'-amino-2'-deoxy-α-D-glucopyranosyl)-sn-glycerol α-AS2

To a solution of 22 (100 mg, 0.15 mmol) in MeOH (5 mL) at room temperature was added NaOMe until pH came up to 9. The mixture was stirred overnight, neutralized with Amberlite IR120H$^+$ exchange resin, filtered, and evaporated under vacuum to afford a white solid, which was directly dissolved in MeOH (5 mL) and to the solution was added dropwise 10 wt % of Pd/C (20 mg). After stirring under the atmosphere of hydrogen for 2 h, the mixture was filtered and then evaporated to dryness. The resulting residue was purified by flash chromatography (DCM/MeOH, 5:1) to afford α-AS2 as a white solid (62 mg, 81%); R$_f$ 0.18 (DCM/MeOH, 5:1); [α]$^{25}_D$ 44.6° (c 0.1, MeOH); $^1$H NMR (500 MHz, CD$_3$OD): δ=5.36 (d, 1H, J=5.1, H-1), 3.95 (ddd, J=11.0, 5.5, 3.2, 1H), 3.81 (dd, J=12.0, 2.3, 1H), 3.72 (dd, J=12.0, 5.4, 1H), 3.54 (ddd, J=15.4, 8.4, 4.8, 3H), 3.47-3.41 (m, 6H), 3.34-3.31 (m, 1H), 3.07 (dd, 1H, J=10.4, 5.1, H-2), 2.84-2.76 (m, 2H, SCH$_2$), 1.58-1.52 (m, 2H), 1.29 (d, J=17.5, 31H, OCH$_2$CH$_2$(CH$_2$)$_{13}$CH$_3$), 0.88 (t, J=7.0, 3H, CH$_2$CH$_3$); $^{13}$C NMR (126 MHz, CD$_3$OD): δ=87.17 (C-1), 81.30, 74.89, 72.66, 72.29, 72.18, 62.46, 57.99, 56.67 (C-2), 33.28, 33.07, 30.77, 30.73, 30.58, 30.46, 27.24, 23.73, 14.42 (CH$_2$CH$_3$); HRMS: calcd for C$_{26}$H$_{53}$NO$_6$SNa$^+$ 530.3491. Found 530.3510 [M+Na]$^+$.

2-Phthalimido-2-deoxy-β-D-glucopyranoside tetraacetate (21)

To a solution of D-Glucosamine hydrochloride (1.00 g, 4.64 mmol) in 1 M NaOH solution (10.0 mL) was added phthalic anhydride (2.96 g, 20.00 mmol). After stirring overnight, the mixture was evaporated to dryness. The resultant syrup was dissolved in pyridine (10.0 mL), and acetic anhydride (3.0 mL) and DMAP (50 mg) were added slowly. After stirring overnight, the reaction mixture was evaporated to dryness, and the resulting residue was purified by flash chromatography (hexane/EtOAc, 1:1) to yield 21 as a yellow solid (1.48 g, 67%); R$_f$ 0.37 (hexane/EtOAc, 1:1); $^1$H NMR data were in agreement with those reported earlier.[25]

1-O-Hexadecyl-2-O-methyl-3-S-(2'-phthalimido-2'-deoxy-3',4',6'-tri-O-acetyl-β-D-glucopyranosyl)-sn-glycerol (23)

To a solution of 19 (100 mg, 0.29 mmol) and 21 (230 mg, 0.48 mmol) in dry dichloromethane (10 mL) was added boron trifluoride-diethyl ether (0.25 mL, 2.00 mmol). After stirring overnight, the reaction mixture was washed with saturated NaHCO$_3$ solution and water, dried over Na$_2$SO$_4$, and concentrated under reduced pressure. The residue was purified by flash chromatography (hexane/EtOAc, 4:1) to afford 23 (144 mg, 65%) as a yellow solid; R$_f$ 0.17 (hexane/EtOAc, 4:1); $^1$HNMR (300 MHz, CDCl$_3$): δ=7.94-7.83 (m, 2H), 7.81-7.72 (m, 2H), 5.85 (dd, J=10.1, 9.2, 1H), 5.55 (d, J=10.6, 1H), 5.21 (dd, J=23.3, 13.3, 1H), 4.38 (dd, J=16.6, 6.1, 1H), 4.34-4.25 (m, 1H), 4.19 (dd, J=12.3, 2.2, 1H), 3.90 (ddd, J=10.1, 4.8, 2.3, 1H), 3.52-3.44 (m, 3H), 3.37 (d, J=5.6, 5H), 2.93 (dd, J=13.7, 5.5, 1H), 2.74 (dd, J=13.7, 5.6, 1H), 2.16-2.08 (m, 3H), 2.03 (d, J=9.4, 3H), 1.88 (s, 3H), 1.60-1.48 (m, 2H), 1.26 (s, 29H), 0.89 (t, J=6.7, 3H); $^{13}$C NMR (75 MHz, CDCl$_3$): δ=170.65, 170.09, 169.50, 134.42, 123.52, 81.71, 79.64, 75.96, 71.73, 71.51, 70.83, 68.91, 62.38, 62.16, 57.69, 53.85, 31.93, 31.15, 29.71, 29.49, 29.37, 26.08, 22.70, 20.76, 20.64, 20.46, 14.13; EIMS: calcd for C$_{40}$H$_{61}$NO$_{11}$SNa$^+$ 787.0. Found 786.5 [M+Na]$^+$.

1-O-Hexadecyl-2-O-methyl-3-S-(2'-amino-2'-deoxy-β-D-glucopyranosyl)-sn-glycerol β-AS2

100 mg of 23 (0.13 mmol) was directly dissolved in 33 wt % of MeNH$_2$/EtOH (5 mL), and the resulting mixture was heated to reflux and stirred overnight, and then evaporated to dryness. The resulting residue was purified by flash chromatography (DCM/MeOH, 3:1) to afford β-AS2 as a white solid (37 mg, 56%); R$_f$ 0.27 (DCM/MeOH, 3:1); [α]$^{25}_D$-32.4° (c 0.1, MeOH); $^1$H NMR (300 MHz, CD$_3$OD): δ=4.41 (d, 1H, J=9.8, H-1), 3.88 (d, J=12.0, 1H), 3.73-3.55 (m, 5H), 3.53-3.44 (m, 6H), 3.36 (d, J=8.4, 1H), 2.97 (dd, 1H, J=13.7, 5.4, SCH$_a$), 2.85 (dd, 1H, J=13.8, 5.4, SCH$_b$), 2.70 (d, 1H, J=18.3, H-2), 1.58 (d, J=6.6, 2H), 1.32 (s, 33H, OCH$_2$CH$_2$(CH$_2$)$_{13}$CH$_3$), 0.93 (t, J=6.7, 3H, CH$_2$CH$_3$); $^{13}$C NMR (75 MHz, CD$_3$OD): δ=87.82 (C-1), 82.33, 81.38, 78.92, 72.65, 72.12, 71.66, 62.98, 58.00, 57.74 (C-2), 49.87, 49.58, 49.30, 49.02, 48.73, 48.45, 48.17, 33.09, 31.85, 30.79, 30.59, 30.48, 27.26, 23.75, 14.45 (CH$_2$CH$_3$); ESI-HRMS: called for C$_{26}$H$_{53}$NO$_6$SNa$^+$ 530.3491. Found 530.3487 [M+Na]$^+$.

TABLE 1

Effect of C-Gln on viability of nutator- generated BT-474 stem cell spheroid viability.

| Cell # | [C-Gln] | | |
| --- | --- | --- | --- |
| | 0 µM | 20 µM | 30 µM |
| | Viability (% of control) | | |
| 10K | 100 | 0 | 0 |
| 15K | 100 | 0 | 0 |
| 20K | 100 | 0 | 0 |
| 25K | 100 | 0 | 0 |

BT-474 cancer stem cells were grown for 7 days in ultra low adhesion 6 well plates. The tumorspheres formed were harvested, trypsinised and cell numbers were determined. Different numbers of cells (10K, 15K, 20K and 25K) were dispersed into 48-well plates. The plates were rotated in a nutator in a 5% CO2 incubator for 5 days. The spheroids formed were incubated with C-Gln (0, 20, 30 µM) for 6 days with replenishment of the medium after 4 days. At the end of the incubation, MTS reagent (20% of final volume in the wells) was added to each well and after incubation for 4 h, the contents were transferred to tubes and 10% SDS solution was added to give a final concentration of 2% SDS. The tubes were vortexed until spheroids in controls were solubilized. The absorbance was read at 490 OD. Wells with no cells were treated in an identical manner and the values were used as blanks for the experiment.

TABLE 2

Effect of Galactosamine-GAEL and Mannosamine GAEL on the viability of BT-474 cancer stem cell spheroids.

| | [ ] µM | | | |
| --- | --- | --- | --- | --- |
| | 0 | 10 | 20 | 30 |
| | Viability (% 0f control) | | | |
| α-Galn | 100 | 9.64 | 0 | 0 |
| β-Galn | 100 | 153.7 | 48.0 | 32.16 |
| α-Mann | 100 | 134.3 | 58.84 | 25.9 |

Equal numbers of BT474 cancer stem cells were seeded into 24-well ultra-low adhesion plates and grown for 6 days to form spheroids. The spheroids were incubated with different concentrations of alpha -or beta galactosamine- or alpha mannoseamine-GAEL for an additional 6 days. The viavbility of the cells were determined by the MTS assay

The invention claimed is:

1. A method of treating a cancer that is refractory to treatment with existing apoptosis-inducing agents comprising administering to an individual having a cancer comprising cancer stem cells that are refractory to treatment with existing apoptosis-inducing agents an effective amount of a compound selected from the group consisting of:

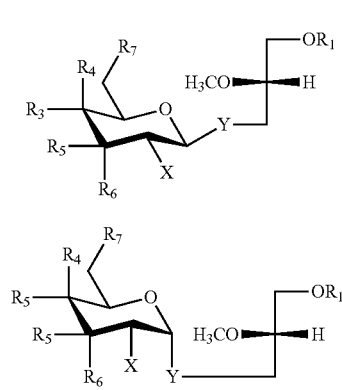

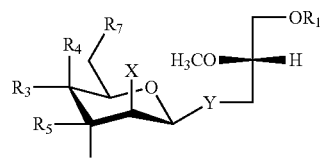

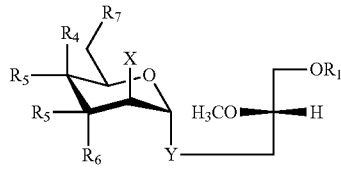

X = OH, NH$_2$, N$_3$, NHR$_8$, NHC(NH)NH$_2$, or N(R$_9$)$_3^+$
Y = O, S, Si(R$_{10}$)$_2$, CH$_2$, or NCOR$_2$
R$_1$ = C$_n$H$_{2n+1}$; C$_n$H$_{2n-1}$; C$_n$H$_{2n-3}$; or C$_n$H$_{2n-5}$; wherein n is an integer ranging from 10 to 30
R$_2$ = C$_1$-C$_{30}$ alkyl, benzyl, or aryl
R$_3$ = H and R$_4$ = OH or H or else
R$_3$ = OH or H and R$_4$ = H
R$_5$ = OH or H and R$_6$ = H or else
R$_5$ = H and R$_6$ = OH or H;
R$_7$ = OH, H, NH$_2$, NHC(NH)NH$_2$, N(R$_9$)$_3^+$;
R$_8$ = alkyl, benzyl, or aryl;
R$_9$ = C$_1$-C$_{10}$ alkyl;
R$_{10}$ = H, alkyl, benzyl, or aryl;

said compound inhibiting development of the cancer stem cells into tumorspheres and causing the disintegration of the cancer stem cells, thereby causing total loss of viability of the cancer stem cells in the individual.

2. The method according to claim 1 wherein the compound is selected from the group consisting of:

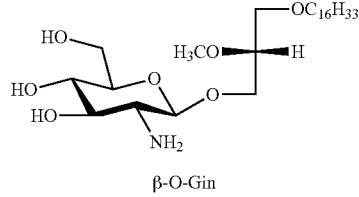

β-O-Gln

β-AO1 (R$_1$ = C$_{16}$H$_{33}$, Y = O; X = NH$_2$,
R$_6$ = H, R$_5$ = OH, R$_4$ = H, R$_3$ = OH,
R$_7$ = OH)

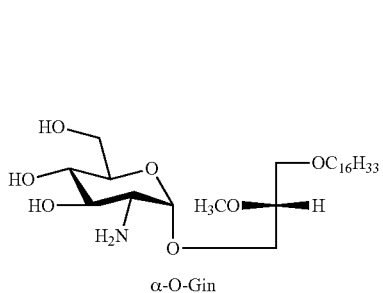

α-O-Gln

α-AO2 (R$_1$ = C$_{16}$H$_{33}$, Y = O; X = NH$_2$,
R$_6$ = H, R$_5$ = OH, R$_4$ = H, R$_3$ = OH,
R$_7$ = OH)

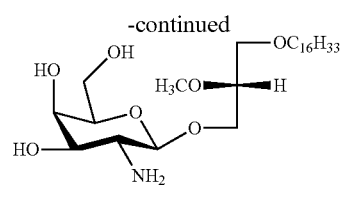

β-O-Gain

β-BO1 ($R_1 = C_{16}H_{33}$, Y = O; X = $NH_2$,
$R_6$ = H, $R_5$ = OH, $R_4$ = OH, $R_3$ = H,
$R_7$ = OH)

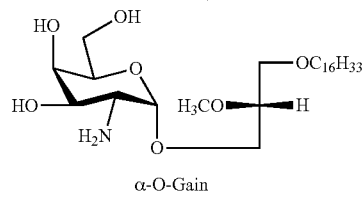

α-O-Gain

α-BO2 ($R_1 = C_{16}H_{33}$, Y = O; X = $NH_2$,
$R_8$ = H, $R_5$ = OH, $R_4$ = OH, $R_3$ = H,
$R_7$ = OH)

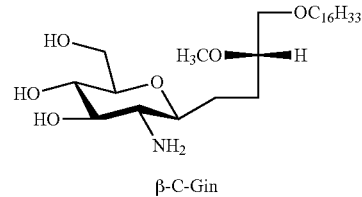

β-C-Gin

β-AC1 ($R_1 = C_{16}H_{33}$, Y = $CH_2$; X = $NH_2$,
$R_6$ = H, $R_5$ = OH, $R_4$ = H, $R_3$ = OH,
$R_7$ = OH)

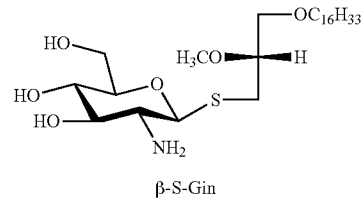

β-S-Gin

β-AS1 ($R_1 = C_{16}H_{33}$, Y = S; X = $NH_2$,
$R_6$ = H, $R_5$ = OH, $R_4$ = H, $R_3$ = OH,
$R_7$ = OH)

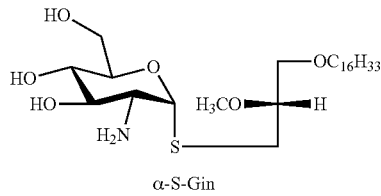

α-S-Gin

α-AS2 ($R_1 = C_{16}H_{33}$, Y = S; X = $NH_2$,
$R_6$ = H, $R_5$ = OH, $R_4$ = H, $R_3$ = OH,
$R_7$ = OH)

3. The method according to claim 2 wherein the cancer is selected from the group consisting of breast cancer, prostate, pancreatic cancer, ovarian cancer, small cell lung cancer and brain cancer.

4. The method according to claim 2 wherein the cancer is a recurring cancer.

5. The method according to claim 2 wherein the cancer is a metastasized or advanced stage cancer.

6. The method according to claim 2 wherein the compound is selected from the group consisting of α-AO2; αBO2; β-AC1; and βAO-1.

7. The method according to claim 1 wherein the cancer is breast cancer.

8. The method according to claim 3 wherein the cancer is breast cancer.

9. The method according to claim 6 wherein the cancer is breast cancer.

10. The method according to claim 1 wherein the tumor stem cell is contacted with the compound at a concentration of 10 μM or greater.

11. The method according to claim 2 wherein the tumor stem cell is contacted with the compound at a concentration of 10 μM or greater.

12. The method according to claim 6 wherein the tumor stem cell is contacted with the compound at a concentration of 10 μM or greater.

13. The method according to claim 7 wherein the tumor stem cell is contacted with the compound at a concentration of 10 μM or greater.

14. The method according to claim 1 wherein the compound is administered in combination with an apoptosis-inducing agent.

15. The method according to claim 2 wherein the compound is administered in combination with an apoptosis-inducing agent.

16. The method according to claim 6 wherein the compound is administered in combination with an apoptosis-inducing agent.

17. The method according to claim 7 wherein the compound is administered in combination with an apoptosis-inducing agent.

18. The method according to claim 1 wherein the cancer is breast cancer.

19. The method according to claim 1 wherein the cancer that is refractory to treatment is treated by killing cancer stem cells.

* * * * *